United States Patent [19]
Wellinghoff et al.

[11] Patent Number: 5,914,120
[45] Date of Patent: Jun. 22, 1999

[54] AMINE-CONTAINING BIOCIDAL COMPOSITIONS CONTAINING A STABILIZED CHLORITE SOURCE

[75] Inventors: Stephen T. Wellinghoff, San Antonio; Joel J. Kampa, Boerne, both of Tex.

[73] Assignee: Southwest Research Institute, San Antonio, Tex.

[21] Appl. No.: 08/924,684

[22] Filed: Sep. 5, 1997

Related U.S. Application Data

[63] Continuation-in-part of application No. 08/426,039, Jun. 5, 1995, abandoned.

[51] Int. Cl.⁶ .................................................. A01N 25/08
[52] U.S. Cl. ...................... 424/406; 424/405; 424/412; 424/413; 424/414; 424/415; 424/485; 424/486
[58] Field of Search ................................ 424/405, 406, 424/409–421, 484, 486

[56] References Cited

U.S. PATENT DOCUMENTS

| | | | |
|---|---|---|---|
| 2,071,625 | 2/1937 | Haas et al. | 99/172 |
| 2,482,891 | 9/1949 | Aston | 252/187 |
| 2,546,568 | 3/1951 | Taylor | 99/150 |
| 2,558,942 | 7/1951 | Eagleson | 167/30 |
| 3,183,057 | 5/1965 | Marks et al. | 21/58 |
| 3,585,147 | 6/1971 | Gordon | 252/187 |
| 3,591,515 | 7/1971 | Lovely | 252/187 |
| 3,767,787 | 10/1973 | Segal | 424/76 |
| 4,104,190 | 8/1978 | Hartshorn | 252/187 R |
| 4,330,531 | 5/1982 | Alliger | 424/149 |
| 4,499,077 | 2/1985 | Stockel et al. | 424/149 |
| 4,504,442 | 3/1985 | Rosenblatt et al. | 422/37 |
| 4,547,381 | 10/1985 | Mason et al. | 426/316 |
| 4,585,482 | 4/1986 | Tice et al. | 106/15.05 |
| 4,681,739 | 7/1987 | Rosenblatt et al. | 422/37 |
| 4,689,169 | 8/1987 | Mason et al. | 252/186.24 |
| 4,728,498 | 3/1988 | Theeuwes | 422/29 |
| 4,748,904 | 6/1988 | Razeto et al. | 99/467 |
| 4,829,129 | 5/1989 | Kelley | 525/326.9 |
| 4,880,638 | 11/1989 | Gordon | 424/662 |
| 4,889,654 | 12/1989 | Mason et al. | 252/100 |
| 4,891,216 | 1/1990 | Kross et al. | 424/78 |
| 4,925,645 | 5/1990 | Mason | 423/477 |
| 4,956,184 | 9/1990 | Kross | 424/661 |
| 4,975,109 | 12/1990 | Friedman, Jr. et al. | 71/67 |
| 4,986,990 | 1/1991 | Davidson et al. | 424/665 |
| 5,078,908 | 1/1992 | Ripley et al. | 252/187.21 |
| 5,126,070 | 6/1992 | Leifheit et al. | 252/186.36 |
| 5,252,343 | 10/1993 | Kross | 424/661 |
| 5,306,440 | 4/1994 | Ripley et al. | 252/186.33 |
| 5,360,609 | 11/1994 | Wellinghoff | 514/772.3 |
| 5,384,134 | 1/1995 | Kross et al. | 424/661 |
| 5,387,350 | 2/1995 | Mason | 210/754 |
| 5,399,288 | 3/1995 | Marzouk et al. | 252/186.21 |
| 5,405,549 | 4/1995 | Pitochelli | 252/187.21 |

FOREIGN PATENT DOCUMENTS

| | | |
|---|---|---|
| 0 287 074 | 4/1988 | European Pat. Off. . |
| 0 611 162 | 2/1994 | European Pat. Off. . |
| 0 611 163 | 2/1994 | European Pat. Off. . |
| 57/198775 | 12/1982 | Japan . |
| 60/092759 | 5/1985 | Japan . |
| 4/164005 | 6/1992 | Japan . |
| 6-107971 | 4/1994 | Japan . |
| 2151138 | 12/1984 | United Kingdom . |
| WO 85/04107 | 3/1985 | WIPO . |
| WO 88/09176 | 5/1988 | WIPO . |
| WO 96/18300 | 6/1996 | WIPO . |

OTHER PUBLICATIONS

Second College Edition, The American Heritage Dictionary, p. 79. No Date.

Hackh's Chemical Dictionary, 2nd Ed., P. Blakiston's Son & Co. Inc., p. 41. No Date.

The Condensed Chemical Dictionary, 9th Ed., Van Nostrand Reinhold Co., p. 40. No Date.

*Primary Examiner*—Neil S. Levy
*Attorney, Agent, or Firm*—Senniger, Powers, Leavitt & Roedel

[57] ABSTRACT

A composite for retarding, killing, preventing or controlling microbiological contamination includes a hydrophilic material containing an α-amino ether, α-amino alcohol or α-amino ester and a chlorite salt, and a hydrophobic material containing an acid releasing agent. The hydrophilic and hydrophobic materials are adjacent and substantially free of water, and the hydrophilic material is capable of generating and releasing chlorine dioxide after hydrolysis of the acid releasing agent.

15 Claims, 11 Drawing Sheets

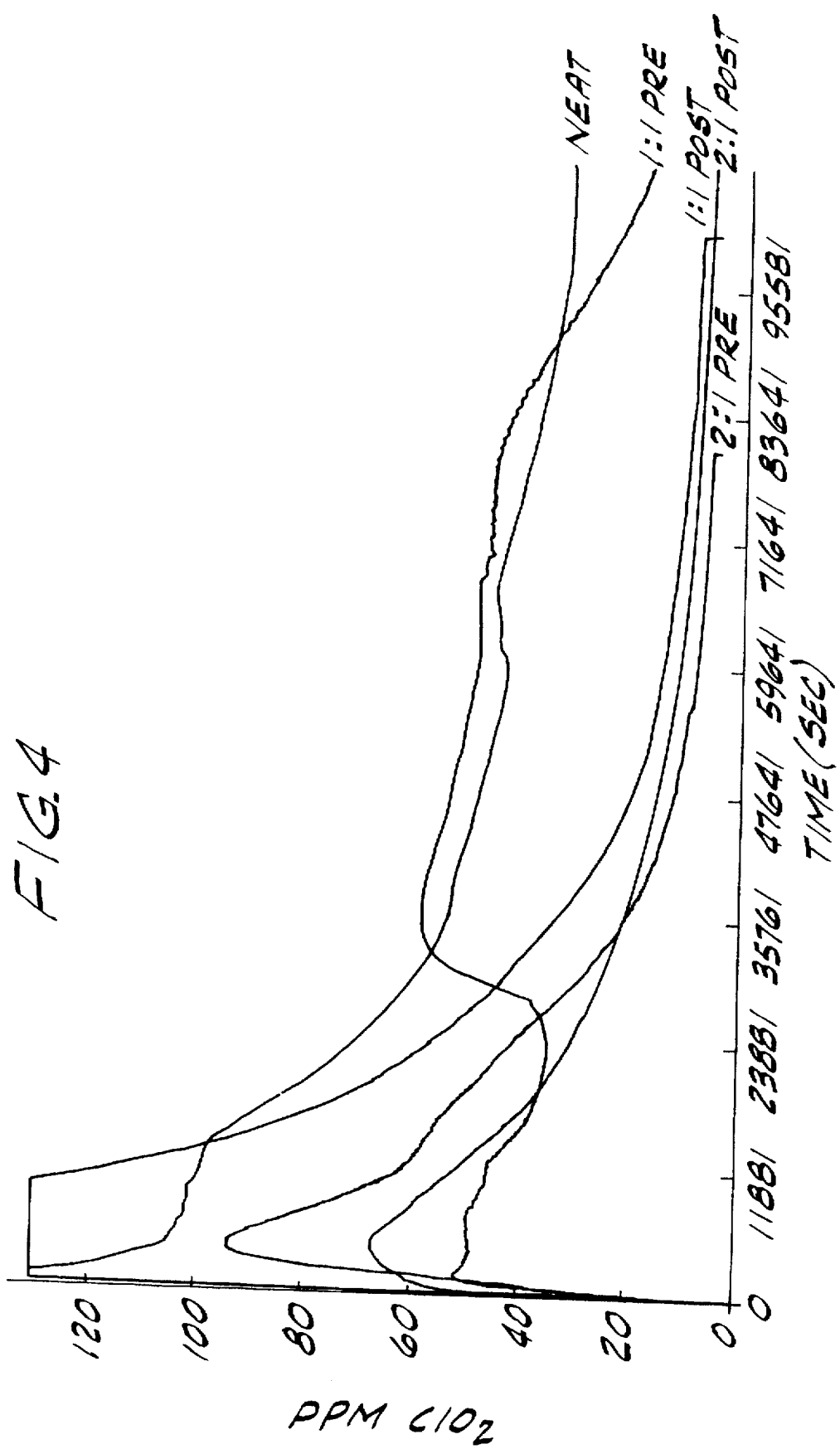

AMINE-CONTAINING BIOCIDAL COMPOSITIONS CONTAINING A STABILIZED CHLORITE SOURCE

REFERENCE TO RELATED APPLICATIONS

This application is a continuation-in-part of U.S. patent application Ser. No. 08/426,039, filed Jun. 5, 1995, now abandoned.

BACKGROUND OF THE INVENTION

The present invention relates generally to a biocidal composition that provides sustained release of chlorine dioxide. The invention particularly relates to such a composite including an amine-containing hydrophilic material having improved long term storage stability for retarding, controlling, killing or preventing microbiological contamination (e.g., bacteria, fungi, viruses, mold spores, algae, and protozoa), deodorizing and/or retarding, preventing or controlling chemotaxis by release of chlorine dioxide.

Chlorine dioxide ($ClO_2$) is a superior oxidizing agent widely used as a bleach, disinfectant, fumigant or deodorizer. It can penetrate the cell wall or membrane and cytoplasm of mold spores, bacteria and other microbiological contaminants at concentrations below one part per million and destroy them.

The incorporation of chlorine dioxide or sodium chlorite in food packaging has prompted studies to determine whether residual levels of such preservatives result in a significant genetic or carcinogenic hazard to humans. Meier et al. studied the effect of subchronic and acute oral administration of chlorine, chlorine dioxide, sodium chlorite and sodium chlorate on the induction of chromosomal aberrations and spermhead abnormalities in mice [Environ. Mutagenesis, 7, 201 (1985)]. Only the highly reactive hypochlorite resulted in a weak positive effect for mutagenic potential. The other compounds, including chlorine dioxide and sodium chlorite, failed to induce any chromosomal aberrations or increased numbers of micronuclei in the bone marrow of mice. Vilagines et al. attribute the relatively innocuous effect of chlorine dioxide to its inability to produce halomethanes, unlike hypochlorite and chlorine [Proc. AWWA Disinfect. Semin., 24 pp. (1977); Chem. Abs. 93, 173513f]. Recently, Richardson et al. reported that an extensive study of the reaction of chlorine dioxide with water borne organics by the Environmental Protection Agency confirmed this observation [Environ. Sci. Technol., 28, 592 (1994)].

Japanese Kokai Nos. 63/296,758, 63/274,434, and 57/168,977 describe deodorants containing chlorine dioxide incorporated in a polymer, ceramic beads, or calcium silicate wrapped in nonwoven cloth, respectively. Gels which generate chlorine dioxide for use as topical applications for disinfection are disclosed by Kenyon et al., Am. J. Vet. Res., 45(5), 1101 (1986). Chlorine dioxide generating gels are generally formed by mixing a gel containing suspended sodium chlorite with a gel containing lactic acid immediately prior to use to avoid premature chlorine dioxide release. Chlorine dioxide releasing gels have also been used in food preservation.

Encapsulation processes have also been used in preparing sources of chlorine dioxide. Canadian Patent No. 959,238 describes generation of chlorine dioxide by separately encapsulating sodium chlorite and lactic acid in polyvinyl alcohol and mixing the capsules with water to produce chlorine dioxide.

Tice et al., U.S. Pat. No. 4,585,482 describe gradual hydrolysis of alternating poly(vinyl methyl ethermaleic anhydride) or poly(lactic-glycolic acid) to generate acid which can release chlorine dioxide from sodium chlorite. A polyalcohol humectant and water are encapsulated with the polyanhydride or polyacid in a nylon coating. After sodium chlorite is diffused into the capsule through the nylon wall, an impermeable polystyrene layer is coacervated around the nylon capsule. Solvents are required for reaction and application of the capsules. The capsules can be coated onto surfaces to release chlorine dioxide. Although the capsules are said to provide biocidal action for several days to months, chlorine dioxide release begins immediately after the capsules are prepared. The batchwise process used to prepare the capsules also involves numerous chemical reactions and physical processes, some of which involve environmental disposal problems.

Powders that release chlorine dioxide as soon as they are prepared have been formed by mixing acid solids and chlorite solids. Lovely, U.S. Pat. No. 3,591,515 describes a chlorite-containing powder that releases chlorine dioxide upon being admixed with an acidcontaining powder. Hartshorn, U.S. Pat. No. 4,104,190 describes solid mixtures of sodium chlorite and citric, adipic or malic acid that are compressed to form tablets. Mason et al., U.S. Pat. Nos. 4,547,381 and 4,689,169 disclose mixtures of powdered sodium chlorite, acid and inert diluent that release chlorine dioxide without exposing the mixtures to ambient moisture. Tice et al., U.S. Pat. No. 4,585,482 describe solid admixtures of sodium chlorite and polylactic acid.

Wellinghoff et al. have formulated composites that include a hydrophobic phase containing an acid releasing agent and a hydrophilic phase containing chlorite or other anions. The composite is substantially free of water and gas (e.g., chlorine dioxide) until it is exposed to moisture. Once exposed to moisture, acid and hydronium ions are generated in the hydrophobic phase. The hydronium ions migrate to the hydrophilic phase and react with the anions to generate a gas such as chlorine dioxide from the composite. These composites are composed of and generate only substances used in foods or substances generally recognized as safe or inert substances. The composites can be used for food packaging and other applications where the substances can be ingested by or in contact with humans or animals. These composites are described in U.S. Pat. Nos. 5,360,609, 5,631,300, 5,639,295 and 5,650,446 and U.S. patent application Ser. Nos. 08/858,860, 08/858,859, 08/465,086, 08/461,716, and 08/461,304. U.S. Pat. No. 5,360,609 describes a hydrogen bonded phase containing a dissolved chlorite salt and describes an amine as a polymerization component of the hydrogen bonded phase. The amine and chlorite salt do not react to form an iminium chlorite. Instead, the chlorite salt dissociates into chlorite anions and counterions, and the amine remains intact.

Wellinghoff et al. U.S. patent application Ser. No. 08/462,039 discloses a composite formulated for maximum chlorine dioxide release in which the hydrophilic material contains an α-amino ether, ester or alcohol and a chlorite salt formed by reaction of an iminium chlorite and a base. Iminium chlorite is unstable to nucleophilic attack by the chlorite anion. When the iminium chlorite is reacted with a base, however, the more stable α-amino ether, ester or alcohol and a chlorite salt are formed.

Wellinghoff et al. U.S. patent application Ser. No. 08/726,413 describes a method for maximizing chlorine dioxide release from an amine-containing composite by omitting the chlorite source until the composite is applied to a surface. After application, the composite is exposed to chlorine dioxide gas that either reacts with the amine to form iminium chlorite in situ or reacts with the amine to provide chlorite anions. The composite is then activated in the presence of moisture to release chlorine dioxide. The composite can be exposed to elevated temperatures during processing, storage and application because the hydrophilic material does not contain iminium chlorite or any chlorite anions that could decompose at such temperatures. The method also precludes premature release of chlorine dioxide from the composite.

Wellinghoff European patent publication 611163 describes compositions containing iminium chlorite that are unstable to nucleophilic attack. Iminium chlorite is formed by reacting chlorine dioxide gas with an amine. The chlorine dioxide gas ($ClO_2$) is reduced by extracting an electron from the amine, forming an aminium radical cation and a chlorite counterion ($ClO_2$). The aminium cation quickly converts to an iminium cation by loss of a proton from an adjacent carbon atom and oxidation by another chlorine dioxide molecule.

Barenberg et al. U.S. patent application Ser. No. 08/724,907 and Wellinghoff et al. U.S. patent application Ser. No. 08/858,860 describe numerous methods of using composites such as those disclosed by Wellinghoff et al. to retard bacterial, fungal, and viral contamination and growth of molds on food, produce, meat, and other materials and to deodorize materials such as textiles and storage spaces.

Wellinghoff et al. U.S. patent application Ser. No. 08/651,876 describes transparent compositions that provide sustained release of chlorine dioxide.

There is a need for an inert composition that can be easily activated to initiate chlorine dioxide release in use. A composition that is composed of and generates only substances used in foods, or those generally recognized as safe or inert substances, is particularly needed for food packaging and other applications where the substances can be ingested by or in contact with humans.

SUMMARY OF THE INVENTION

Among the objects of the invention, therefore, may be noted the provision of a composition which releases a concentration of chlorine dioxide sufficient to eliminate bacteria, fungi, molds, algae, protozoa, and viruses; the provision of such a composition which releases such chlorine dioxide concentrations after activation for a period of up to several months; the provision of such a composition which can be stored for a prolonged period and then activated prior to use; the provision of such a composition which increases the release rate of chlorine dioxide in proportion to increased levels of temperature and humidity which promotes mold and bacteria growth; and the provision of such a composition that only releases substances approved for human exposure or ingestion and is relatively inexpensive.

The present invention is directed to a composite for retarding, killing, preventing or controlling microbiological contamination which includes a hydrophilic material containing an α-amino ether, α-amino alcohol, or α-amino ester and a chlorite salt, and a hydrophobic material containing an acid releasing agent. The hydrophilic and hydrophobic materials are adjacent and substantially free of water, and the hydrophilic material is capable of generating and releasing chlorine dioxide after hydrolysis of the acid releasing agent.

Another embodiment of the invention is directed to a composite for retarding, killing, preventing or controlling microbiological contamination which includes a hydrophilic material containing an α-amino ether, α-amino alcohol, or α-amino ester, a chlorite salt, and an amide, and a hydrophobic material containing an acid releasing agent. The hydrophilic and hydrophobic materials are adjacent and substantially free of water, and the hydrophilic material is capable of generating and releasing chlorine dioxide after hydrolysis of the acid releasing agent.

Yet another embodiment of the invention is directed to a hydrophilic composition including urea, a plasticizer selected from the group consisting of N-methylacetamide, formamide, succinamide, N-ethylacetamide, N-methylformamide, N-ethylformamide, acrylamide, isopropylacrylamide-acrylamide, and amido substituted alkylene oxides, and a base selected from the group consisting of a metal alkoxide, an ammonium alkoxide, a metal oxide, a metal carboxylate, and an ammonium carboxylate.

Other objects and advantages of the invention will be apparent from the following detailed description.

BRIEF DESCRIPTION OF THE DRAWINGS

FIG. 4 is a plot of chlorine dioxide release rates for several powder compositions;

DETAILED DESCRIPTION OF THE PREFERRED EMBODIMENTS

Figure 1:
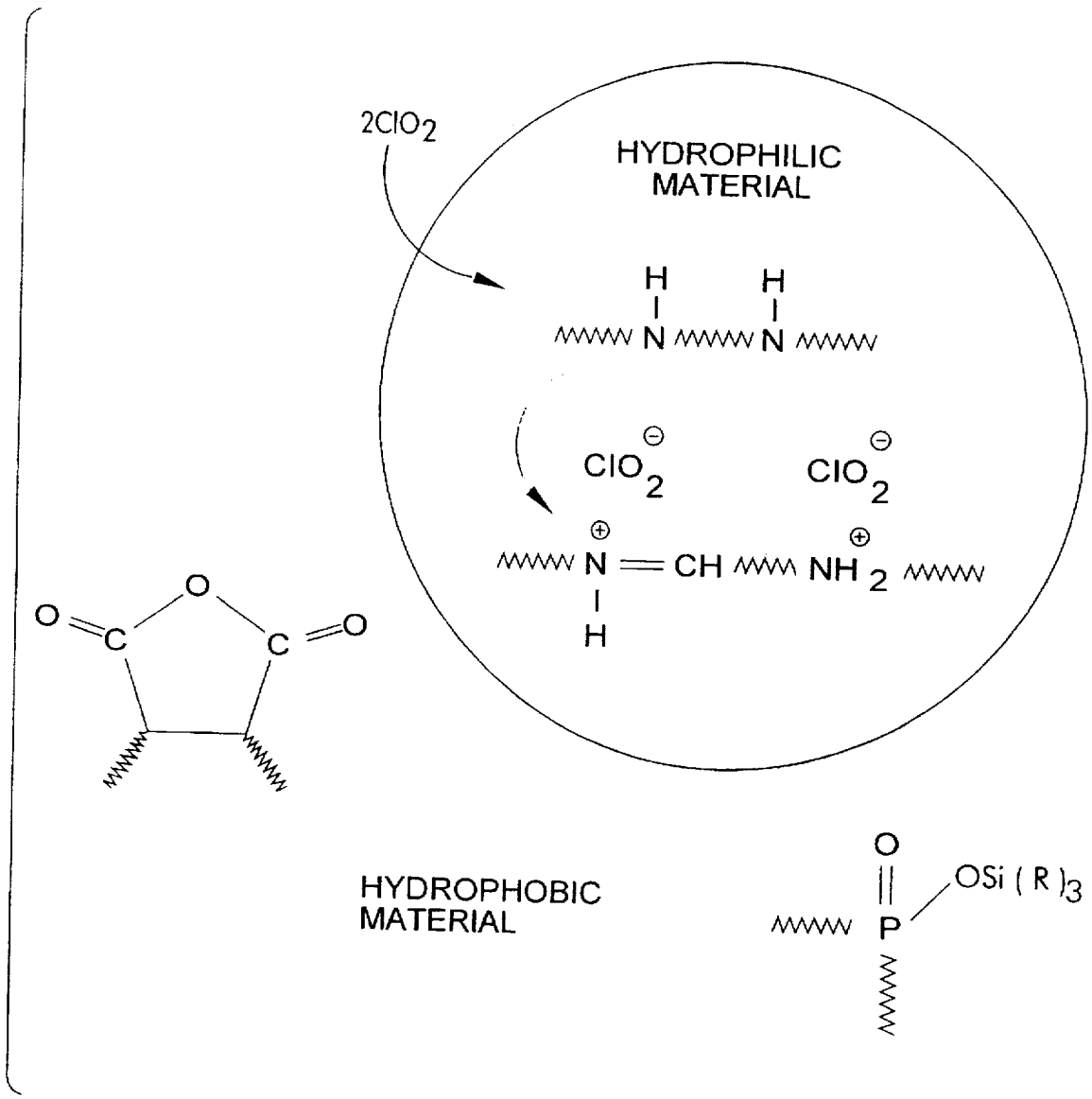
FIG. 1 is a schematic which illustrates conversion of an amine precursor to an iminium chlorite.

In accordance with the present invention, it has been discovered that sustained release of chlorine dioxide can be generated from a composite containing chlorite anions when the composite is exposed to moisture. The composite comprises a hydrophilic material and a hydrophobic material. The composite may be, for example, a dispersion composed of hydrophilic and hydrophobic phases, or a mechanical combination of the hydrophilic and hydrophobic materials, such as powders and adjacent films. The powder has a hydrophobic core embedded with chlorite containing particles. Adjacent films comprise separate layers of the hydrophilic or hydrophobic materials.

Preferably, the composite comprises between about 5.0 wt. % and about 95 wt. % hydrophilic material and between about 5.0 wt. % and about 95 wt. % hydrophobic material, more preferably between about 15 wt. % and about 95 wt. % hydrophilic material and between about 15 wt. % and about 95 wt. % hydrophobic material. The relative proportions of the hydrophilic and hydrophobic materials need only be such that chlorine dioxide is produced and released from the composite. If the composite is a dispersion, either material can form the continuous phase. The continuous phase constitutes between about 15 wt. % and about 95 wt. % of the dispersion and the dispersed phase constitutes between about 5 wt. % and about 85 wt. % of the dispersion, and preferably, the continuous phase constitutes between about 50 wt. % and about 95 wt. % of the dispersion and the dispersed phase constitutes between about 5 wt. % and about 50 wt. % of the dispersion.

The hydrophobic material of the composite can be composed entirely of an acid releasing agent or can comprise the acid releasing agent in combination with a diluent, dispersant and/or a plasticizer. Any acid releasing agent which is capable of being hydrolyzed by ambient moisture is acceptable for purposes of the present invention. Preferably, the acid releasing agent does not react with the hydrophilic material, and does not exude or extract into the environment. The hydrophobic material comprises between about 10 wt. % and about 100 wt. % of the acid releasing agent, up to about 80 wt. % diluent, up to about 20 wt. % dispersant, and up to about 60 wt. % plasticizer, and preferably, between about 40 wt. % and about 100 wt. % of the acid releasing agent, between about 20 wt. % and about 80 wt. % diluent, and up to about 20 wt. % plasticizer.

The hydrophilic material of the composite can be composed entirely of a source of chlorite anions or can comprise the chlorite anion source in combination with another hydrophilic material. The hydrophilic material preferably contains an amine, an amide or an alcohol, or a compound containing amino, amido or hydroxyl moieties and having a high hydrogen bonding density. A source of chlorite anions is incorporated in the hydrophilic material and preferably constitutes between about 2 wt. % and about 40 wt. % of the hydrophilic material in the form of chlorite anions and counterions, and more preferably, between about 8 wt. % and about 10 wt. % of the hydrophilic material. The chlorite anions generally do not react with the hydrophilic material, but are surrounded by hydrogen bonds contributed by the nitrogen or hydroxide within the hydrophilic material.

When the chlorite source is a chlorite salt, the salt dissociates in the hydrophilic material such that the hydrophilic material in the composite will include chlorite anions and counterions.

Suitable chlorite sources that can be incorporated into the hydrophilic material include alkali metal chlorites such as sodium chlorite or potassium chlorite, alkaline-earth metal chlorites such as calcium chlorite, or chlorite salts of a transition metal ion or a protonated primary, secondary, tertiary or quaternary amine such as ammonium chlorite, trialkylammonium chlorite, and quaternary ammonium chlorite. Many chlorite sources, such as sodium chlorite, are stable at processing temperatures in excess of about 100° C., allowing for processing at relatively high temperatures. Chlorine dioxide-releasing composites can be used to deodorize, retard, prevent or control chemotaxis, or to kill, retard, control or prevent the growth of bacteria, molds, fungi, algae, protozoa, and viruses.

It has been found that the acid releasing agent within the hydrophobic material is hydrolyzed by adsorbed moisture. The acid releasing agent is either an acid or a substance that can be hydrolyzed to an acid (i.e., a substance that reacts with the water that diffuses into the hydrophobic layer to form an acid). In either case, the acid in the hydrophobic material dissolves in the water that diffuses into the material, forming hydronium ions and a counterion. The reaction products of this hydrolysis reaction are hydronium ions and counterions when the reaction proceeds to completion, or hydronium ions, counterions, acid and water when the reaction is in equilibrium. The hydronium ions resulting from the acid hydrolysis diffuse from the hydrophobic material into the hydrophilic material, where they react with anions to generate a gas. The gas diffuses out of the composite into the surrounding atmosphere for a period of up to about six months to affect materials situated near the composite. Composites that release at least about $1.0 \times 10^6$ mole gas/cm$^2$ for a period of at least one week, one month or six months can be formulated by the processes of the present invention for a variety of end uses, including deodorization, chemotaxis control, delay or prevention such as reduction of insect infestation, and control, delay, destruction or prevention of the growth of microorganisms such as bacteria, molds, fungi, algae, protozoa, and viruses on materials.

The hydrophobic and hydrophilic materials are substantially free of water to avoid significant release of chlorine dioxide prior to use of the composite. For purposes of the present invention, a hydrophilic material, a hydrophobic material, or a dispersion thereof is substantially free of water if the amount of water in the composite does not provide a pathway for transmission of hydronium ions from the hydrophobic material to the hydrophilic material. Generally, each of the hydrophilic and hydrophobic materials can include up to about 0.1 wt. % water and, more preferably up to about 0.05 wt. % water, without providing such a pathway for interdiffusion between the hydrophilic and hydrophobic materials. Insubstantial amounts of water can hydrolyze a portion of the acid releasing agent to produce acid and hydronium ions within the composite. The hydronium ions, however, do not diffuse into the hydrophilic material until enough free water is present for transport of hydronium ions.

The rate of chlorine dioxide gas release from a composite can be altered in various ways, such as by changing the temperature of the composite, changing the viscosity of the hydrophilic and hydrophobic materials, changing the dispersibility of the hydrophilic and hydrophobic materials, changing the concentration of acid releasing agent in the composite, adding a desiccant or humectant to the composite to control release of gas once the composite is exposed to moisture, adding a buffer to the hydrophobic material to delay release of a gas from the composite, changing the hydrophobicity of the hydrophobic material by changing the nature of the acid generative moiety therein, changing the composite microstructure, substituting alternative hydrophobic materials or anhydrous particles, changing the method of processing the composite, changing the order of addition of ingredients in preparing the composite, or changing the volume fractions of the hydrophilic and hydrophobic materials to produce continuous or discrete phases within a dispersion.

Preferred amides for use as the hydrophilic material include formamide, acrylamide-isopropylacrylamide, and copolymers of formamide and acrylamide-isopropylacrylamide, and copolymers of acrylamide, isopropylacrylamide or N,N-methylene bisacrylamide and a primary amine or a secondary amine. Such amides can be useful vehicles for film casting prior to exposure to chlorine dioxide, which does not react with polymerizable, electron deficient alkenes such as acrylamide.

Suitable amines for use as the hydrophilic material include primary amines, secondary amines, and tertiary amines having pendant hydrogen bonding groups. Tertiary amines having non-hydrogen bonding pendant groups that are dissolved in a hydrophilic solvent are also acceptable. Representative amines include: alkanolamines; copolymers of aminoalkanes and alkene bisacrylamides; alkylaminopyridine; alkene diamines; alkylamino cycloalkanes; alkylamino-carboxyamido alkanes dissolved in a diluent; amines having the formula $R_{3-x}NH_x$; $R_1R_2NCH_2CH_2C(O)NH_2$; solubilized $N(CH_2CH_2OH)_{3-x}H_x$, $R_3N(NCH_2CH_2C(O)NH_2)_2$, $(CH_3)_2N(CH_2)_z(CH_3)_2$, $R_5R_6N(CH_2)_zNHC(O)NH_2$,

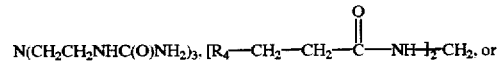

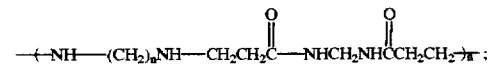

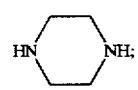

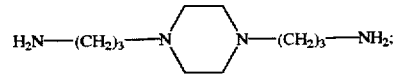

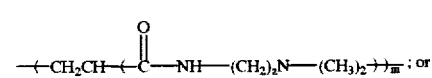

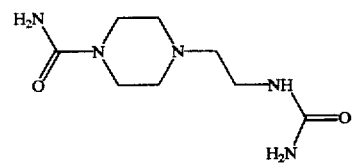

wherein: R substituents are, independently, $-(CH_2CH_2O)_yH$, $-C(CH_3)_2(CH_2)_zOH$, $-(CH_2)_zNH(CH_2CH_2O)_zH$, $-CH(CH_3)_2$,

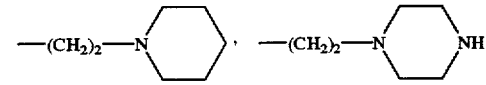

,alkyl, cycloalkyl, benzyl, acrylamide, or pyridyl; $R_1$, $R_2$, $R_5$, and $R_6$ are alkyl; $R_3$ is straight chain $C_6$ to $C_{12}$ alkyl; $R_4$ is cycloalkyl or benzyl; m is 1–100; n is 2 or 3; x is 0, 1 or 2; y is 1 or 2; and z is 1–6. Generally, the above compounds can be solubilized in formamide, isopropylacrylamide-acrylamide or other conventional plasticizers.

Preferred amines include monoethanolamine, diethanolamine, triethanolamine, a copolymer of 1,3-diaminopropane or 1,2-diaminoethane and N,N-methylene bisacrylamide, 4-dimethylaminopyridine, tetramethylene ethylene diamine, N,N-dimethylamino cyclohexane, solubilized 1-(N-dipropylamino)-2-carboxyamido ethane or 1-(N-dimethylamino)-2-carboxyamido ethane, a primary amine having the formula $R_1NH_2$, a secondary amine having the formula $R_2R_3NH$, $N(CH_2CH_2OH)_3$,

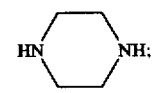

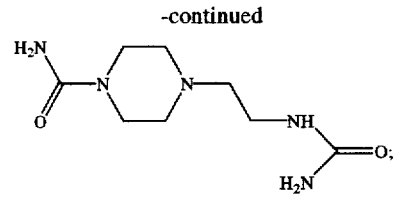

solubilized $NR_5R_6R_7$, $(CH_3)_2NCH_2CH_2N(CH_3)_2$, $R_8R_9NCH_2CH_2C(O)NH_2$, $R_{10}N(NCH_2CH_2C(O)NH_2)_2$, $R_{11}R_{12}N(CH_2)_3NHC(O)NH_2$, $N(CH_2CH_2NHC(O)NH_2)_3$,

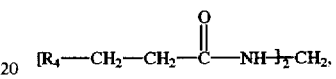

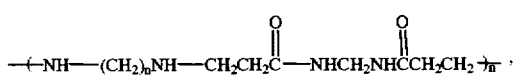

or

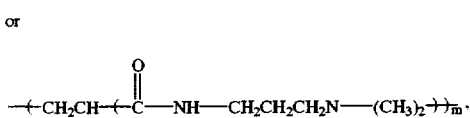

wherein: $R_1$ is $-CH_2CH_2OCH_2CH_2OH$, $-C(CH_3)_2CH_2OH$, $-CH_2CH_2NHCH_2CH_2OH$, $-CH(CH_3)_2$, $-CH_2CH_2OH$

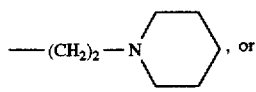, or

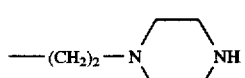

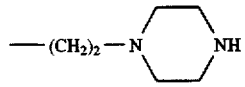

$R_2$ and $R_3$ are, independently, hexyl, benzyl, n-propyl, isopropyl, cyclohexyl, acrylamide, or $-CH_2CH_2OH$; $R_4$ is cyclohexyl or benzyl; $R_5$ and $R_6$ are methyl; $R_7$ is cyclohexyl or 4-pyridyl; $R_8$ and $R_9$ are, independently, methyl, n-propyl or isopropyl; $R_{10}$ is n-$C_6H_{13}$ or n-$Cl_{12}H_{25}$; $R_{11}$ and $R_{12}$ are, independently, methyl, ethyl, n-propyl or isopropyl; m is an integer from 1 to 100; and n is 2 or 3. Suitable diluents include formamide or acrylamide-isopropyl acrylamide. Oligomeric or polymeric secondary amines converted to acrylamide substituted tertiary amines by Michael reaction with acrylamides are also suitable because the amide group does not react with the acid releasing agent.

Hydroxylic compounds, including ethylene glycol, glycerin, methanol, ethanol, methoxyethanol, ethoxyethanol, or other alcohols, can be used as the hydrophilic material. However, gas release can occur very rapidly when a hydroxylic compound is incorporated in the composite and can limit the applications for such composites to rapid gas releasing systems.

Suitable acid releasing agents include carboxylic acids, esters, anhydrides, acyl halides, phosphoric acid, phosphate esters, trialkylsilyl phosphate esters, dialkyl phosphates, sulfonic acid, sulfonic acid esters, sulfonic acid chlorides, phosphosilicates, phosphosilicic anhydrides, carboxylates of poly α-hydroxy alcohols such as sorbitan monostearate or sorbitol monostearate, and phosphosiloxanes. Examples of such acid releasing agents include an anhydride or phosphate ester blended with or grafted to polypropylene, polyethylene or polystyrene, or trimethylsilyl phosphate esters of the formulae

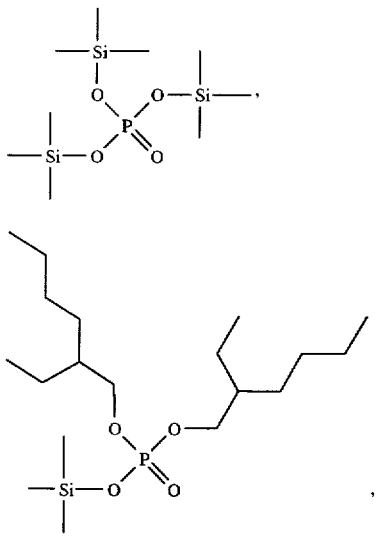

$(R_2)_{4-n}Si(OR_1)_n$ or $(CH_3)_3SiOP(O)(OR)_2$ wherein R is a non-hydrogen bonding group, alkyl or aryl, $R_1$ and $R_2$ are alkyl, alkoxy or aryl, and n is an integer from 1 to 25.

Linear or star like oligomers (e.g., a micelle like molecule with a lipid wall and a P—O—Si core), such as a phosphosilicic anhydride that is the reaction product of a phosphoric acid ester of a $C_4$ to $C_{27}$ organic compound and a silicate ester, are preferred acid releasing agents because they can be melt- or solvent-processed with the option of being crosslinked after processing to provide film stability. Preferred phosphosilicic anhydrides of esters have the formula

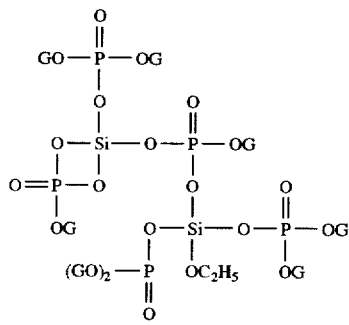

wherein G is a carboxylic acid ester of a polyhydric alcohol and a $C_4$ to $C_{27}$ hydrocarbon, which has the formula

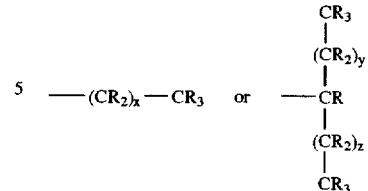

wherein each R is individually selected from hydrogen, hydroxy, alkyl, alkenyl, or —OC (O)R'; R' is a $C_4$ to $C_{27}$ alkyl or $C_4$ to $C_{27}$ alkenyl; x is an integer from 1 to 30; y is an integer from 0 to 30; and z is an integer from 0 to 30. Particularly preferred phosphosilicic anhydrides of polyol based esters include alkylene glycol fatty acid ester acid releasing waxes such as propylene glycol monostearate acid releasing wax having the formula

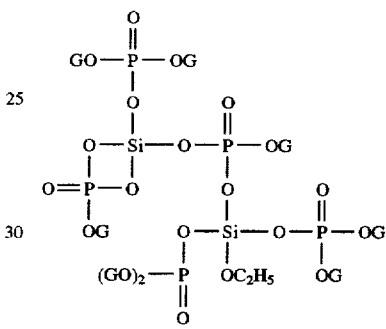

wherein G is

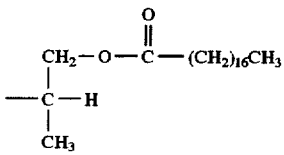

A preferred phosphosilicic anhydride of a glycerol based ester, known as LPOSI or glycerol monostearate acid releasing wax, has the formula

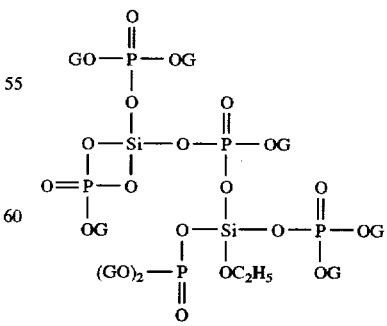

wherein G has the formula

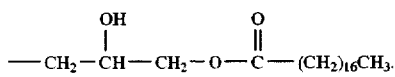

Other preferred acid releasing agents have the formulae:

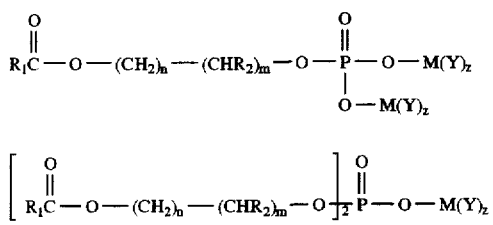

wherein M(Y)z is an oligomeric radical in which Y is a portion of a multifunctional oxide structure and M is a group IIIA, IVA, or IVB element such as titanium, aluminum, tin, or silicon; R1 is an alkyl group; R2 is methyl, ethyl, propyl, a methyl amido, or an ethyl amido group; m is 0, 1, 2 or 3; n is 0, 1, 2 or 3; and z is 2 or 3.

Acid anhydrides are also preferred acid releasing agents and include organic acid anhydrides, mixed organic acid anhydrides, homopolymers of an organic acid anhydride or a mixed inorganic acid anhydride, and copolymers of an organic acid anhydride or a mixed inorganic acid anhydride with a monomer containing a double bond. Preferred mixed inorganic acid anhydrides contain a phosphorus-oxygen-silicon bond. Preferred anhydrides include copolymers of maleic anhydride, methacrylic anhydride, acetic anhydride, propionic anhydride, or succinic anhydride, and vinyl, styrene or an alkene, such as maleic anhydride-styrene copolymers, or grafts thereof with olefins such as polypropylenes, polyethylenes, or polystyrenes. Copolymers of acid anhydrides and esters of lactic or glycolic acids can provide a rapid initial gas release rate followed by a slow release rate.

The hydrophobic material can further include a diluent such as microcrystalline wax, paraffin wax, synthetic wax such as chlorinated wax or polyethylene wax, an oligomer, or a polymer such as atactic polypropylene, polyolefin, or polyester, or polymer blends, multicomponent polymers such as copolymers or terpolymers, or polymer alloys thereof. The diluents are commercially available from various sources. Preferred microcrystalline waxes include the Petrowax microcrystalline waxes commercially available from Astor Wax Corp., Doraville, Ga. Diluents can be included in the hydrophilic material as well. Plasticizers can also be incorporated in either the hydrophobic or hydrophilic materials as is known in the art. Generally, formamide, isopropylacrylamide-acrylamide, N-methylacetamide, succinamide, N-ethylacetamide, N-methylformamide, N-ethylformamide, and amido substituted alkylene oxides are acceptable plasticizers.

The dispersant in the hydrophobic material is any substance that controls release of chlorine dioxide gas from the composite, lowers the surface reactivity of the hydrophilic material, and does not react with the hydrophilic material. Substances having hydrophilic and hydrophobic portions are preferred. The hydrophilic portion of the substance can be absorbed by the surface of the hydrophilic material. Preferred dispersants that can be incorporated into the hydrophobic material have a melting point not greater than 150° C., and include amides of carboxylates such as amide isostearates, polyvinyl acetates, polyvinyl alcohols, polyvinylpyrrolidone copolymers, and metal carboxylates such as zinc isostearate. Suitable polyvinylpyrrolidone copolymers include copolymers of polyvinylpyrrolidone and hexadecane such as Ganex V-216, and copolymers of polyvinylpyrrolidone and eicosene such as Ganex V-220, which are commercially available from GAF Corp.

The hydrophobic material preferably includes a microcrystalline wax diluent and an acid releasing wax, such as propylene glycol monostearate acid releasing wax. The preferred phosphosilicic anhydride acid releasing waxes are generally prepared by melting a carboxylic acid ester of a polyhydric alcohol, admixing phosphorus pentoxide into the melt, then admixing a silicate or silane into the melt, and cooling to solidify the resulting acid releasing wax. The carboxylic acid ester of a polyhydric alcohol is preferably a glycerol ester or glycol ester such as an alkylene glycol carboxylate (e.g., propylene glycol monostearate, glycerol monostearate, or glycerol distearate). Propylene glycol monostearate is most preferred because it does not foam excessively or obstruct nozzles or other fluid transport equipment when preparing the acid releasing wax or the composite or when incorporating the composite into polymer films or other materials as end products. A substance that is capable of reacting with the silicate or silane to form P—O—Si or C(O)—O—Si bonds in the acid releasing wax can be substituted for phosphorus pentoxide, such as monostearyl diethylphosphate. A process for preparing a phosphosilicic anhydride acid releasing wax using monostearyl diethylphosphate can be performed with reference to Ralph Iler, "Chemistry of Silica: Solubility, Polymerization, Colloid and Surface Properties in Biochemistry," J. Wiley & Sons, N.Y., p. 297 (1979). Preferred silicates or silanes include tetraalkylsilicates such as tetraethyl orthosilicate, alkyl silanes, and monoalkoxy silanes. The preparation of representative acid releasing waxes is described in Examples 8, 17 and 18 below.

A moisture scavenger, such as sodium sulfate, calcium sulfate, ferrous sulfate, magnesium sulfate, calcium chloride, moisture-depleted silica gel, alumina, zeolites such as dehydrated crystalline zeolites, synthetic amorphous zeolites, and permutites, clays such as bentonite and kaolin, potassium permanganate, molecular sieves and oxygen-scavenging salts, can be added to the composite to prevent premature hydrolysis of the acid releasing agent in the hydrophobic material.

Conventional film forming additives can be added to the hydrophobic and hydrophilic materials as needed. Such additives include crosslinking agents, flame retardants, emulsifiers and compatibilizers.

In a preferred embodiment, a composite for retarding, killing, preventing or controlling microbiological contamination comprises a hydrophobic material containing an acid releasing agent and a diluent, and a hydrophilic material containing chlorite anions. The hydrophilic and hydrophobic materials are adjacent and substantially free of water, and the hydrophilic material is capable of generating and releasing chlorine dioxide after hydrolysis of the acid releasing agent.

In another preferred embodiment, a composite for retarding, killing, preventing or controlling microbiological contamination comprises a hydrophobic material containing an acid releasing agent, and a hydrophilic material containing chlorite anions and an amine, an amide, an alcohol, or a compound containing amino, amido or hydroxyl moieties. The hydrophilic and hydrophobic materials are adjacent and substantially free of water, and the hydrophilic material is capable of generating and releasing chlorine dioxide after hydrolysis of the acid releasing agent.

In yet another preferred embodiment, a dispersion for retarding, killing, preventing or controlling microbiological contamination comprises a hydrophobic continuous phase containing an acid releasing agent, and a hydrophilic dispersed phase containing chlorite anions. The hydrophilic dispersed phase and the hydrophobic continuous phase are substantially free of water, and the hydrophilic dispersed phase is capable of generating and releasing chlorine dioxide after hydrolysis of the acid releasing agent. In a similar embodiment a dispersion for retarding, killing, preventing or controlling microbiological contamination comprises a hydrophobic dispersed phase containing an acid releasing agent, and a hydrophilic continuous phase containing chlorite anions. The hydrophilic continuous phase and the hydrophobic dispersed phase are substantially free of water, and the hydrophilic continuous phase is capable of generating and releasing chlorine dioxide after hydrolysis of the acid releasing agent.

It is also preferred to prepare a composite for retarding, killing, preventing or controlling microbiological contamination comprised of a hydrophobic material containing an acid releasing agent selected from the group consisting of phosphoric acid, a trialkylsilyl phosphate ester, a dialkyl phosphate, sulfonic acid, a sulfonic acid chloride, a homopolymer of a mixed inorganic acid anhydride, a phosphosilicate, a phosphosilicic anhydride, a carboxylate of a poly α-hydroxy alcohol, a phosphosiloxane, a copolymer of an organic acid anhydride with a monomer containing a double bond, a copolymer of a mixed inorganic acid anhydride with a monomer containing a double bond, and a mixed inorganic acid anhydride containing a phosphorus-oxygen-silicon bond, and a hydrophilic material containing chlorite anions. The hydrophilic and hydrophobic materials are adjacent and substantially free of water, and the hydrophilic material is capable of generating and releasing chlorine dioxide after hydrolysis of the acid releasing agent.

Preferred Chlorine Dioxide Releasing Composites

Composites for release of chlorine dioxide are formulated by dissociation of a chlorite salt in a hydrophilic material as described above. An example of such a composite is formed by dissolving sodium chlorite in an amide. When the hydrophilic material contains an amine, the composite can also be formed by exposing the hydrophilic material to chlorine dioxide gas that either reacts with the amine to provide chlorite anions and counterions, or reacts with the amine to form an iminium chlorite in situ if the oxidation potential of the amine is sufficiently low for the amine to be oxidized.

FIG. 1 illustrates preparation of a composite containing iminium chlorite. The amine hydrophilic material is in contact with a hydrophobic acid releasing agent (both hydrolyzed P—O—Si and maleic anhydride are shown in FIG. 1). Chlorine dioxide (ClO$_2$) is reduced by extracting an electron from the amine, forming an aminium radical cation (not shown) and a chlorite counterion (ClO$_2^-$). The aminium cation quickly converts to an iminium cation by loss of a proton from an adjacent carbon atom and oxidation by another chlorine dioxide molecule. The mechanism for above reaction in an aqueous system is described by Rosenblatt et al., J. Org. Chem., 28, 2790 (1963); J. Amer. Chem. Soc. 89(5), 1158, 1163 (1967). A general reaction scheme for formation of iminium chlorite from an amine and chlorine dioxide gas is shown below:

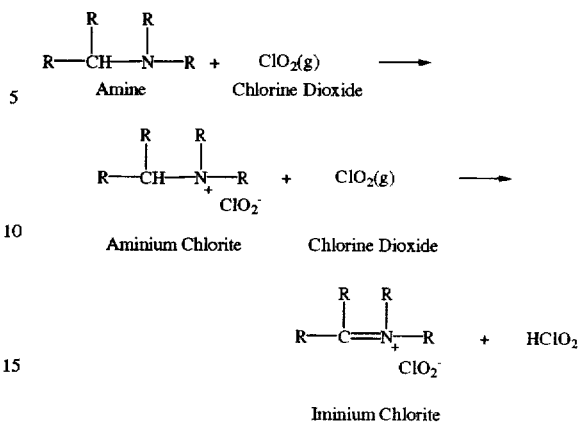

High chlorine dioxide to chlorite conversions are obtained if the chlorite anion and/or iminium cation that is generated by the initial electron transfer from the amine are rapidly complexed and stabilized by a hydrophilic molecule. In some formulations, uncomplexed chlorite anion may be depleted by subsequent reactions with the iminium counterion at temperatures above about 60° C. Chlorites are also subject to disproportionation into chloride and chlorate. An amine with a high pK$_a$ is preferred because it reacts more rapidly with chlorine dioxide and acts as a more effective proton sink, maintaining the basic pH required for chlorite ion stability.

Figure 2:
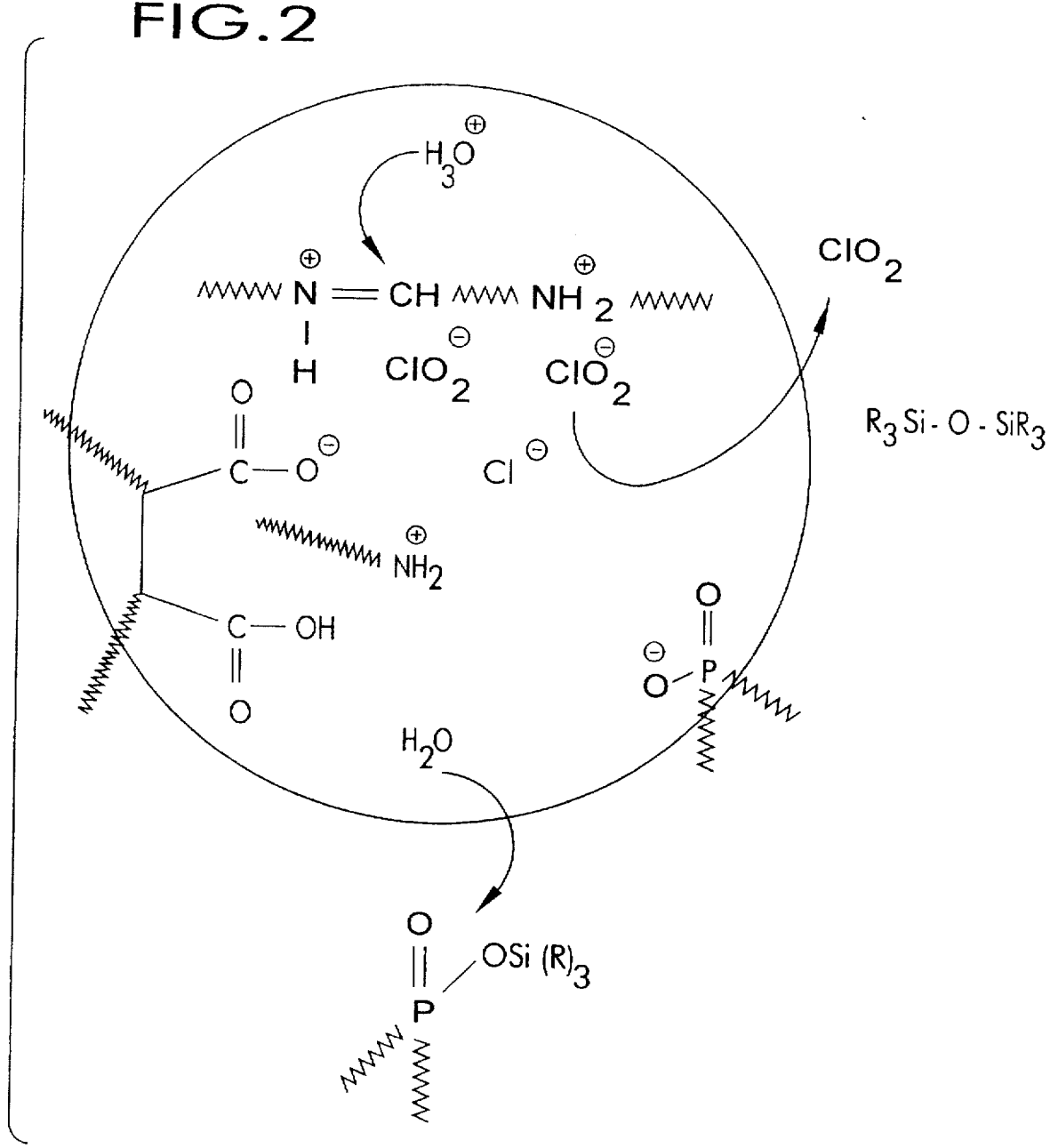
FIG. 2 illustrates hydrolysis of an acid anhydride in a hydrophobic phase and migration of hydronium ion to the iminium chlorite to release chlorine dioxide gas.
Figure 3A:
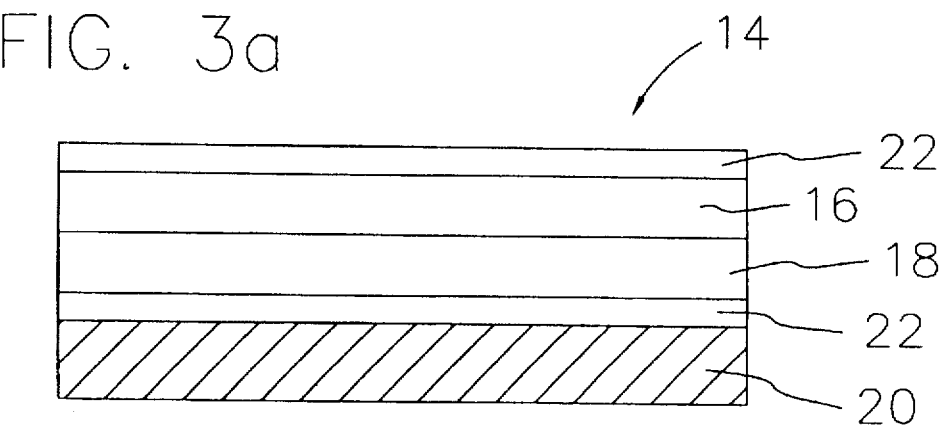
FIGS. 3a, 3b and 3c are schematics of multilayered composites for providing sustained release of chlorine dioxide.
Figure 3B:
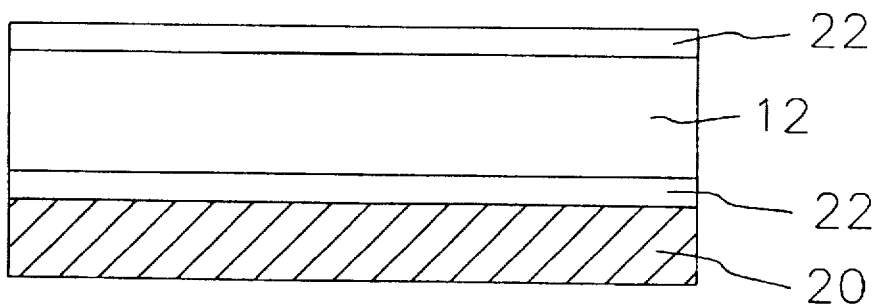
Figure 3C:
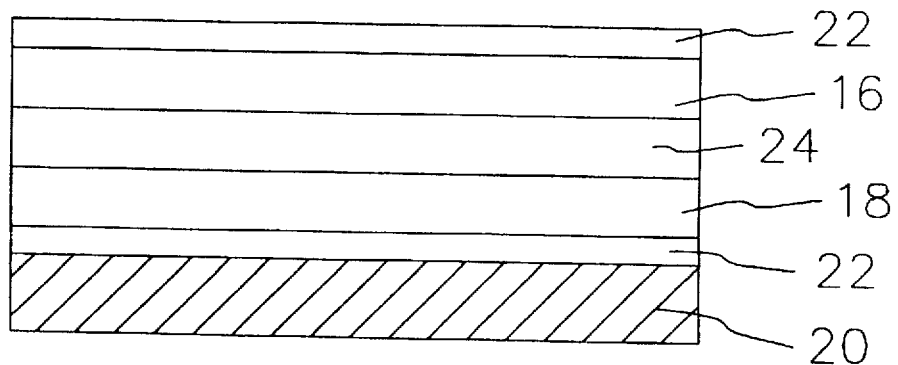

FIG. 2 illustrates the mechanism for release of chlorine dioxide from iminium chlorite when moisture contacts the composite. Hydrolysis of the acid releasing agent provides hydronium cations (H$_3$O$^+$) which diffuse from the hydrophobic material to the hydrophilic material containing iminium chlorite. The hydronium cations react with iminium chlorite to release chlorine dioxide gas. The decomposition products of the reaction are an aminium cation (shown as

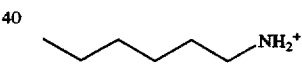

in FIG. 2), a carboxylate (COO$^-$, not shown in FIG. 2), and Cl$^-$. These products are retained within the composite.

In order for an amine to form iminium chlorite in neat form or in the presence of a plasticizer, the amine must be sufficiently electron rich and the amine nitrogen must be locally mobile. Otherwise, the chlorine dioxide will dissolve in the amine rather than form iminium chlorite. An amine substituted with electron donating groups that donate electrons to convert chlorine dioxide to chlorite is preferred. Electron withdrawing groups concentrate electron density at such groups such that it is difficult for the chlorine dioxide to extract an electron from the amine. Electron withdrawing groups should be separated from the amine center by at least two methylene groups in order for the chlorine dioxide to extract an electron from the amine. Movement of the bonds about the nitrogen center of the amine is required for aminium formation. If the amine is frozen into a glassy matrix, the amine nitrogen will not be mobile and the amine will not convert to iminium chlorite. A glassy amine can be softened to increase mobility by adding at least about 10 wt. % of a plasticizer, such as a low molecular weight amide, to the amine to lower glass transition temperature below the reaction temperature. Other suitable plasticizers are well known in the polymer art.

It has been found that, in some instances, iminium chlorite may decompose if the composite is exposed to temperatures exceeding about 60° C., reducing the available chlorite concentration for conversion to chlorine dioxide. In order to maximize chlorine dioxide release from the composite, it has been discovered that the chlorite source can be omitted from the composite until the composite is applied to a surface when the hydrophilic material in the composite is an amine. After application, the composite is exposed to chlorine dioxide gas which either reacts with the amine to form iminium chlorite in situ or reacts with the amine to provide chlorite anions. The composite is then activated in the presence of moisture to release chlorine dioxide. This method enables the composite to be exposed to elevated temperatures during processing, storage and application as compared to the temperatures at which the iminium chlorite decomposes, because the hydrophilic material does not contain iminium chlorite or any chlorite anions. The method also precludes premature release of chlorine dioxide from the composite. Chlorine dioxide can be provided on site by passing the composite through a chlorine dioxide generator.

Conventional chlorine dioxide generators generate an atmosphere of chlorine dioxide that is saturated with water. Chlorine dioxide which comes into contact with the composite of the invention must first be dissolved into a material that does not absorb water such as a low melting hydrocarbon wax or chlorohydrocarbon wax. Alternatively, chlorine dioxide is dried with a desiccant. Chlorine dioxide is thus delivered from a wet industrial process into the composite without exposing the composite to water.

Such a composite is prepared by mixing a hydrophilic material containing an amine with a hydrophobic material containing an acid releasing agent to form a mixture, and exposing the mixture to chlorine dioxide that reacts with the amine to form iminium chlorite within the hydrophilic material. The hydrophilic and hydrophobic materials are substantially free of water, and the hydrophilic material is capable of generating and releasing chlorine dioxide after hydrolysis of the acid releasing agent. The mixture can be applied to a substrate to form a film before exposure to chlorine dioxide, such as when the mixture is applied as a tacky hot melt at a temperature below that at which the mixture will decompose. The film can be exposed to chlorine dioxide by contacting the film with a gaseous chlorine dioxide atmosphere. The chlorine dioxide can be dissolved in an organic solvent that does not absorb water before being exposed to the film, such as microcrystalline wax, paraffin wax, synthetic wax such as chlorinated wax or polyethylene wax, or a polymer such as atactic polypropylene, polyolefin, or polyester, or polymer blends, multicomponent polymers such as copolymers or terpolymers, or polymer alloys thereof. The film is exposed to moisture after the film is contacted with chlorine dioxide to hydrolyze the acid releasing agent and release chlorine dioxide from the film.

Alternatively, the composite can be prepared by providing a hydrophilic material containing an amine and a hydrophobic material containing an acid releasing agent, the hydrophilic and hydrophobic materials being adjacent, and exposing the adjacent materials to chlorine dioxide that reacts with the amine to form iminium chlorite within the hydrophilic material. The hydrophilic and hydrophobic materials are substantially free of water, and the hydrophilic material is capable of generating and releasing chlorine dioxide after hydrolysis of the acid releasing agent. The hydrophilic and hydrophobic materials can be applied to a substrate to form a film before exposure to chlorine dioxide. These materials can be applied to the substrate as separate films.

Maximum chlorine dioxide release from a composite can also be achieved by stabilizing the chlorite anion. Iminium chlorite is unstable to nucleophilic attack by the chlorite anion, resulting in reaction products where chlorite is consumed. Such premature decomposition of chlorite reduces the amount of chlorine dioxide available for release during use of the composite. Premature decomposition of chlorite is reported in Example 7 wherein all chlorine dioxide was released from an acidified hydrophilic material after two hours at room temperature.

It has been discovered that the room temperature lifetime of chlorite anion is substantially extended when a strong base is present in the hydrophilic material containing the iminium chlorite. In the absence of water, the iminium chlorite is immediately decomposed into an α-amino ether, α-amino ester or α-amino alcohol and a chlorite salt. The chlorite salt is more stable against nucleophilic attack than an iminium chlorite. In Example 7, chlorine dioxide was released from such stabilized hydrophilic materials for at least 24 hours at room temperature after acidification. Most of the hydrophilic materials tested released at least 60% of the chlorine dioxide within three weeks of acidification. Thus, when a base was added to the hydrophilic material, chlorine dioxide release was sustained for one day to several weeks as compared to only two hours for the less stable hydrophilic material. The mechanism for stabilization of the chlorite counterion is shown below.

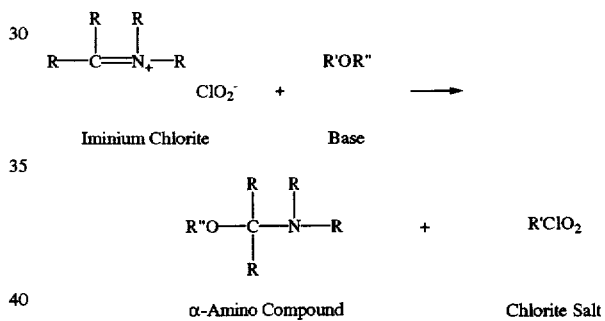

wherein each of the R groups correspond to those of the selected amine, R' is a cation, and R" is hydrogen, an alkyl group or an —C(Q)R$_1$ radical wherein R$_1$ is hydrogen or an alkyl group.

When the base is a metal alkoxide, it reacts with the iminium chlorite to form an α-amino ether as follows.

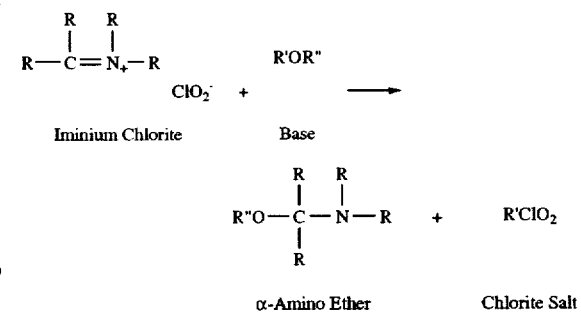

When a metal oxide is used as the base, the metal oxide is hydrolyzed to a metal hydroxide, and the iminium chlorite reacts with the metal hydroxide to form an α-amino alcohol and a chlorite salt as shown below.

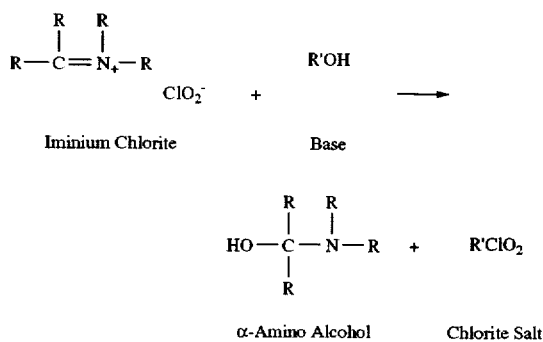

Iminium Chlorite    Base

α-Amino Alcohol    Chlorite Salt

When a carboxylate is used as the base, the iminium chlorite reacts with the carboxylate to form an α-amino ester and a chlorite salt as shown below.

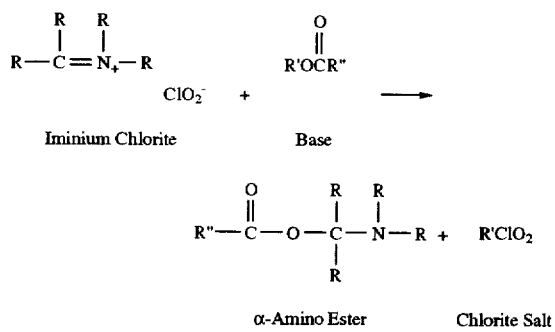

Iminium Chlorite    Base

α-Amino Ester    Chlorite Salt

The composite comprises a hydrophilic material containing an α-amino ether, α-amino ester, or α-amino alcohol and a chlorite salt, and a hydrophobic material containing an acid releasing agent. The hydrophilic and hydrophobic materials are adjacent and substantially free of water, and the hydrophilic material is capable of generating and releasing chlorine dioxide after hydrolysis of the acid releasing agent. The hydrophilic material can also include an amide such as urea.

The composite is prepared by providing a hydrophilic material containing an amine and a base, and a hydrophobic material containing an acid releasing agent, the hydrophilic and hydrophobic materials being adjacent, and exposing the adjacent materials to chlorine dioxide that reacts with the amine to form iminium chlorite which is decomposed by the base to form a chlorite salt within the hydrophilic material. The hydrophilic and hydrophobic materials are substantially free of water, and the hydrophilic material is capable of generating and releasing chlorine dioxide after hydrolysis of the acid releasing agent. The hydrophilic material can include an amide such as urea. The adjacent materials can be applied to a substrate to form a film before exposure to chlorine dioxide, such as when the adjacent materials are applied as a tacky hot melt at a temperature below that at which the materials will decompose. The adjacent materials can also be applied to the substrate as separate films. The film can be exposed to chlorine dioxide by contacting the film with a gaseous chlorine dioxide atmosphere. The chlorine dioxide can be dissolved in an organic solvent that does not absorb water before being exposed to the film, such as microcrystalline wax, paraffin wax, synthetic wax such as chlorinated wax or polyethylene wax, or a polymer such as atactic polypropylene, polyolefin, or polyester, or polymer blends, multicomponent polymers such as copolymers or terpolymers, or polymer alloys thereof. The film is exposed to moisture after the film is contacted with chlorine dioxide to hydrolyze the acid releasing agent and release chlorine dioxide from the film.

Acceptable strong bases for use in stabilizing the chlorite include metal alkoxides such as sodium, potassium or calcium methoxides, ethoxides, propoxides or butoxides, ammonium salts of alkoxides such as trimethylammonium methoxide, metal oxides such as aluminum oxide or sodium oxide, metal carboxylates including sodium or potassium acetates, laurates, and stearates, substituted metal carboxylates, ammonium salts of carboxylic acids such as trimethylammonium acetate, or other materials that would generate a strong basic reaction to attack the nitrogen center of iminium chlorite.

In a hydrophilic material containing a tertiary amine (e.g., 3-dimethylaminopropanamide), N-methylacetamide and urea, iminium chlorite is stabilized by forming an α-amino ether, α-amino ester or α-amino alcohol and a chlorite salt. Any monomeric or oligomeric amide substituted plasticizer, such as succinamide, formamide, or N-methylformamide, N-ethylacetamide, N-ethylformamide, and amido substituted alkylene oxides, can be substituted for N-methylacetamide in order to soften the amine. Formamide and N-methyl formamide are toxic and would not be preferred in applications involving human contact. If the amine center is sufficiently mobile, the addition of a plasticizer is unnecessary. Urea improves the chlorine dioxide uptake and release efficiency of the hydrophilic material because it has a high hydrogen bonding density and will not react with the acid releasing agent. Compounds having a high amide concentration can also be used to improve hydrophilic material efficiency. Preferably, the composite comprises between about 5 wt. % and about 95 wt. % of the hydrophilic material and between about 5 wt. % and about 95 wt. % of the hydrophobic material. The hydrophilic material comprises between about 5 to about 30 wt. % of an amine and between about 70 and about 95 wt. % of a hydrophilic solvent including between about 35 and about 55 wt. % urea, between about 35 wt. % and about 55 wt. % plasticizer and about 10 wt. % base. It has been found that not more than about 0.5 moles of chlorine dioxide per mole of amine should be added to the hydrophilic material or the stability of the material could be compromised.

Formulating Gas-Releasing Composites

The composites of the present invention can be formulated in various ways to accommodate a wide range of end use applications. The composite is generally prepared by dissolving a chlorite salt in a hydrophilic material, and then mixing the hydrophilic material with a hydrophobic material containing an acid releasing agent. The hydrophilic and hydrophobic materials are adjacent and substantially free of water, and the hydrophilic material is capable of generating and releasing chlorine dioxide after hydrolysis of the acid releasing agent. The composite can be applied to a substrate to form a film, such as by applying the composite as a tacky hot melt at a temperature below that at which the anions within the hydrophilic material will decompose.

The composite can be formulated as an extrudate, such as a film or pellets, or as a powder using conventional extrusion and spray drying methods, respectively. When the composite is formulated as a powder, chlorite containing particles are formed by dissolving a chlorite source in a hydrophilic solvent and extruding the solution through nozzles of a spray dryer. Once the solution is transformed into spray dried particles, the particles can be routed to a cyclone separator to isolate small particles preferably having a diameter of between about 5 and about 150 microns. The particles can then be stored in a dry atmosphere. Once the hydrophilic particles are made, they are fed into a fluidized bed. The hydrophobic material containing the acid releasing agent is aerosolized by passing the material through small diameter nozzles into the chamber of the fluidized bed where it can impinge upon the fluidized chlorite-containing particles. Upon contact with the fluidized particles, the chlorine dioxide releasing powder is formed as the hydrophobic material solidifies to form a hydrophobic core having a layer of hydrophilic chlorite-containing particles embedded in the outer surface thereof. Aggregation is minimized because the hydrophilic particles are hard inorganic materials. The particles can then be packaged in a dry sealed container.

Thus, the powders are generally prepared by forming particles containing chlorite anions that are capable of reacting with hydronium ions to generate chlorine dioxide gas, and spraying a hydrophobic material containing an acid releasing agent onto a fluidized bed of the particles so as to form a powder having a core containing the hydrophobic material and a layer of the particles containing chlorite anions on a surface of the core.

In forming the chlorine dioxide releasing powder, anhydrous particles, such as anhydrous sodium sulfate, calcium sulfate, magnesium sulfate, or a moisture depleted silica gel, can be included in the fluidized bed to form a mixture of hydrophilic chlorite-containing particles and anhydrous particles. For purposes of the present invention, an anhydrous material does not contain water, such as adsorbed water or water of crystallization. The anhydrous particles delay release of chlorine dioxide which is catalyzed by atmospheric moisture. The anhydrous particles can also be postmixed with the chlorine dioxide releasing powder to delay chlorine dioxide release.

Although the hydrophilic and hydrophobic materials can be formulated as described above for the composite, it is preferred that the chlorite powder contains an alkali or alkaline-earth chlorite. The hydrophobic material preferably contains microcrystalline wax, paraffin wax, synthetic wax such as chlorinated wax or polyethylene wax, or a polymer such as atactic polypropylene, polyolefin, or polyester, or polymer blends, multicomponent polymers such as copolymers or terpolymers, or polymer alloys thereof. An acid releasing wax, such as the glycerol monostearate acid releasing wax or propylene glycol monostearate acid releasing wax described above, is preferred as the hydrophobic material.

If the acid releasing wax is extruded at a viscosity between about 10 and about 1000 cP through nozzles of between about 1 and about 10 mil diameter, a fine spray of molten wax between about 5 and about 400 microns in diameter is generated.

Thus, a powder of the invention comprises particles containing chlorite anions, and a hydrophobic core having the particles on a surface thereof. The hydrophobic core contains an acid releasing agent. The particles and hydrophobic core are substantially free of water, and the particles are capable of generating and releasing chlorine dioxide after hydrolysis of the acid releasing agent.

The powders of the invention can also be prepared using mechanical blending, mechanical-fluidized blending and other known powder preparation methods, including the powder prepared according to the method disclosed in the copending Wellinghoff et al. U.S. patent application No. 08/858,859, filed May 19, 1997 and entitled "Sustained Release Biocidal Powders," which is incorporated herein by reference.

Powders of the invention are easily prepared and can be used as is or incorporated into various end-use products, such as films, formed objects, adhesives, granular blends, and powdered compositions. The powders can be also be impregnated, melt processed, or otherwise incorporated into a variety of materials to provide films and coatings for a wide range of end use applications.

In addition to formation of powdered composites, the composites of the present invention can be formulated in solvents to allow for film casting or other application methods. The composite can be applied as a film by using well known hot melt, dip coat, spray coat, curtain coat, dry wax, wet wax, and lamination processes.

The composites can also be provided as a layer 12 composed of a microdispersed hydrophobic and hydrophilic material as shown in FIG. **3*b*, or as a multilayered composite 14 including a separate hydrophobic layer 16 and a separate hydrophilic layer 18 as shown in FIG. 3*a*. The hydrophobic and hydrophilic layers can be applied by casting the hydrophilic layer onto a substrate 20 and then casting the hydrophobic layer onto the hydrophilic layer, as illustrated in FIG. 3*a*. The multilayered composite or single layer can be applied in conjunction with moisture regulating layers 22** to control the rate of moisture ingress into the hydrophilic material or hydrophobic material to control chlorine dioxide release from the multilayered composite when activated by moisture.

In order to generate chlorine dioxide in a controlled fashion it is useful to limit the access of water to the hydrophobic layer containing the acid releasing agent and to control the surface area of contact between the layer releasing the hydronium ion and the hydrophilic layer containing chlorite. Such controlled release can be obtained by casting the hydrophobic and hydrophilic materials 16, 18 as separate layers with an intermediate boundary layer 24 that regulates hydronium ion transport between the materials as shown in FIG. **3*c***.

The layered composites of the present invention are intended to maintain a desired rate of chlorine dioxide release (moles/sec/$cm^2$ of film) in the presence of atmospheric moisture at a surface for a length of time required for chlorine dioxide to absorb onto the surface and kill bacteria or other microbiological contaminants. However, leakage from a container or exposed surface reduces the chlorine dioxide concentrations at the surface because of chlorine dioxide diffusion into the atmosphere. The chlorine dioxide concentration released from the film for a chosen time period can be calculated given the leakage rate and the rate of absorbance at a surface. Thus after measuring the leakage rate, the composite is formulated so that it contains a large enough reservoir of chlorite reacting at a speed sufficient to compensate for the leakage rate for the desired time period of sustained release.

Therefore, design of a chlorine dioxide releasing composite suitable for controlled release and biocidal action within a container must take into account several aspects, namely, the chlorine dioxide production rate from the controlled release film, the partitioning of chlorine dioxide between the phases within the container (e.g. gas, liquid and solid phases) in a reversible (absorbed) or irreversible (reacted) fashion, and the leakage rate of gas from the container. Design of such a composite is described in Example 15.

A preferred extended release system of the present invention conserves the chlorite reservoir by emitting a series of periodic pulsed releases timed to coincide with the suspected times of bacterial, viral, fungal or other microbiological contamination or the typical incubation time for the biological of interest. The system design can be optimized to maintain the desired kill concentration for the requisite time at the atmospheric chlorine dioxide leakage rates imposed by the specific application.

A typical controlled release multilayered composite includes water swellable films A and B of a thickness of about 5 mil with a hydrophobic layer A and a hydrophilic layer B as described above for the composite. The hydrophobic layer A contains an acid releasing agent such as an anhydride and hydronium ions generated by anhydride hydrolysis. The hydrophilic layer B contains chlorite anions as provided, for example, by dissolving sodium chlorite or another chlorite source in a hydrophilic solvent. The hydrophobic and hydrophilic layers are separated by a water swellable intermediate layer C having a thickness 1 (typically about 5 mil) and diffusion constant, D. The effective ion concentrations applied to the boundaries of intermediate layer C by the layers A and B are a strong function of the water transport properties of layer C.

The intermediate layer C can be composed of a wide variety of materials since chlorine dioxide can diffuse equally well in both hydrophobic and hydrogen bonded matrices. Such materials include polyionomers such as protonated and neutralized, sulfonated, or phosphorylated oligo- or poly-alkenes such as polyethylene, polypropylene, alkyl acrylates and copolymers thereof. Lipid substituted polyhydroxy alcohol phosphates and phosphosilicates and their mixtures with alkene polymers and oligomers are also preferred. Finely divided anhydrous salts or desiccants may be added to any of the layers to retard the reaction to chlorine dioxide that is catalyzed by water.

It has been discovered that construction of a multilayered composite wherein the arrangement of the layers in the composite is defined by the formula $C(ACB)_nC$ (wherein n represents the desired number of pulses) provides periodic pulsed release of high concentrations of chlorine dioxide over several weeks or months. Such pulsed release can be coordinated to the growth, incubation and contamination of viruses, molds, fungi and bacteria. The cycle time and peak concentrations of chlorine dioxide would be controlled by the layer thickness, chlorite and anhydride loading, and the water and ionic permeation characteristics of layers A, B and C. Pulsed release occurs as each layer $(ACB)_i$ is successively penetrated by water vapor and hydronium ions. Structures of type CDC can also be made where D is a mixture or emulsion of A and B of a phase size of between about 0.2 and about 100 microns. The materials of construction for the CDC composites can be the same as those used in making the $C(ACB)_nC$ composites. Additionally, a multilayered composite $C(DCD)_nC$ can be made in order to provide pulsed release as described above.

Pulsed releases of chlorine dioxide that vary from about one day to over about 200 days can be achieved for 5 mil thick A, B and C films by separating the hydrophobic layer A containing the acid releasing agent from the hydrophilic layer B containing chlorite anions by an intermediate layer C capable of supporting varying hydronium ion transport rates.

The pulsed release capabilities of a multiple layered film can be calculated as provided in Example 16.

In a preferred embodiment, a multilayered composite for providing sustained release of a gas such as chlorine dioxide comprises a hydrophobic layer containing an acid releasing agent, and a hydrophilic layer containing anions such as chlorite anions. The hydrophilic and hydrophobic layers are adjacent and substantially free of water, and the hydrophilic layer is capable of generating and releasing a gas such as chlorine dioxide after hydrolysis of the acid releasing agent. When a surface of the hydrophilic layer and a surface of the hydrophobic layer are in contact, the hydrolysis and gas release occur after contact of the surfaces is made. An intermediate layer can be present between the hydrophilic layer and the hydrophobic layer to control diffusion of water into the hydrophobic layer or the diffusion of hydronium ions produced from the hydrolysis into the hydrophilic layer, so as to control the rate of gas release. A moisture regulating layer can be in contact with one or more surfaces of the hydrophobic layer to control the rate of moisture ingress into the hydrophobic layer. In one embodiment, a first moisture regulating layer is in contact with a surface of the hydrophobic layer and a second moisture regulating layer is in contact with a surface of the hydrophilic layer to control the rate of moisture ingress into the hydrophobic layer. The hydrophilic layer, the hydrophobic layer, or the intermediate layer can contain an anhydrous salt or a desiccant to delay the hydrolysis.

Another multilayered composite of the invention for providing sustained release of a gas comprises a layer comprising a hydrophobic phase containing an acid releasing agent and a hydrophilic phase containing chlorite anions, and a moisture regulating layer in contact with a surface of the layer, such that moisture permeating the moisture regulating layer hydrolyzes the acid releasing agent to initiate release of chlorine dioxide from the multilayered composite. The hydrophilic and hydrophobic phases are interdispersed and substantially free of water. A second surface of the layer can be in contact with a second moisture regulating layer. Preferably, the layer is a dispersion having a phase size of between about 0.2 microns and about 100 microns.

Another multilayered composite for providing time pulsed release of chlorine dioxide comprises at least one hydrophobic layer containing an acid releasing agent, at least one hydrophilic layer containing chlorite anions, and at least three barrier layers to control the diffusion of water into the hydrophobic layer or the diffusion of hydronium ions produced by hydrolysis of the acid releasing agent into the hydrophilic layer. The arrangement of the layers in the composite is defined by the formula $C(ACB)_nC$ wherein C is a barrier layer, A is a hydrophobic layer, B is a hydrophilic layer, and n is an integer ranging from 1 to 10. The hydrophilic layer, the hydrophobic layer, or the barrier layers can contain an anhydrous salt or a desiccant to delay the hydrolysis.

Applications for Gas-Releasing Composites

Applications for the composites are numerous. The composites can be used in most any environment where exposure to moisture will occur.

Chlorine dioxide-releasing composites can be used to retard, kill, prevent or control microbiological contamination on a surface of a material, within the material or in the atmosphere surrounding the material by exposing a surface of a material to a composite that does not release chlorine dioxide gas in the absence of ambient moisture, and exposing the surface to moisture to generate and release the gas from the composite into the atmosphere surrounding the surface. In an alternative embodiment, microbiological contamination is retarded, killed, prevented or controlled on a surface of a material, within the material or in the atmosphere surrounding the material by placing the material adjacent a composite that does not release chlorine dioxide gas in the absence of ambient moisture, and exposing the composite to moisture to release the gas from the composite into the atmosphere surrounding the material.

The chlorine dioxide-releasing composites can also be used to deodorize a surface of a material or the atmosphere surrounding the material by exposing a surface of a material to a composite that does not release chlorine dioxide in the absence of ambient moisture, and exposing the surface to moisture to generate and release the gas from the composite into the atmosphere surrounding the surface. In another embodiment, a surface of a material or the atmosphere surrounding the material is deodorized by placing the material adjacent to a composite that does not release chlorine dioxide in the absence of ambient moisture, and exposing the composite to moisture to release the gas from the composite into the atmosphere surrounding the material.

The chlorine dioxide-releasing composites can also be used to retard, prevent or control chemotactic attraction of an organism to a material by exposing a surface of a material to a composite that does not release chlorine dioxide gas in the absence of ambient moisture, and exposing the surface to moisture to generate and release the gas from the composite into the atmosphere surrounding the surface. In another embodiment, chemotactic attraction of an organism to a material is retarded, prevented or controlled by placing the material adjacent to a composite that does not release chlorine dioxide gas in the absence of ambient moisture, and exposing the composite to moisture to release the gas from the composite into the atmosphere surrounding the material.

In the above methods, the surface of the material can be impregnated with the composite, the composite can be admixed with the material, the composite can be enclosed within a gas-permeable container, or the material and the composite can be enclosed within a container. When the composite is enclosed within a container, the container can be hermetically sealed, or partially sealed such that some gas leaks from the container.

The surface or material that is exposed to the composite can be a portion of a container or part of a substrate placed within the container upon which the composite has been coated as a film or otherwise applied. The biocidal atmosphere generated within the container can be used in storing food products including blueberries, raspberries, strawberries, and other produce, ground beef patties, chicken filets, seafood, and other meats, enhanced foods, pet foods, dry foods, cereals, grains, or most any food subject to bacterial contamination or mold growth. Bar soap, laundry detergent, stored paper documents, clothing, paint, and seeds can be protected from mold growth. Medical instruments, devices and supplies as well as disposable or nondisposable personal care products can be sterilized to prevent microbial contamination. Medical or biological waste can also be sterilized to kill microbials within the waste. Odors from athletic shoes, disposable footwear, and refuse can also be minimized when they are contained within a treated container. Conventional containers can be used such as paperboard or containerboard boxes, corrugated, nonwoven, plastic, or polymeric multilaminate containers, cellulosic, plastic or paper bags, seed packets, or waste containers. The composites of the invention can also be included in an adhesive or ink or on a label applied to a container.

The treated surface can be a reusable or disposable mat or sheet including a dental tray covering, a surgical tray covering, a shower mat, nonwoven bandage material, a meat cutting board, a liner for drawers or shelves, an insert for athletic bags or gym lockers, a food wrapper, a paper sheet for separating hamburger patties, a meat packaging tray, an overpouch such as those used in packaging intravenous bags, a fresh fruit separator or box liner, an absorbent pad for poultry, meat, seafood or produce, or an absorbent layer for use in diapers. Such mats or sheets are typically made from paper, cellulosic, polymeric, woven fabric or nonwoven materials.

Such a method can also be used to coat the surface of a seed to protect the seed from molds and fungi during storage and to protect against mycotic growth when the seed is planted. The coating, when activated by moisture, creates a microatmosphere of chlorine dioxide in the soil in the vicinity of the seed and inhibits mycotic growth that normally would impede seed germination. This coating has no effect upon the germination of the seeds. Seeds in storage do not have to be physically coated to be protected but rather can be in a closed container containing the active material as a packet, "tea bag" or coating on the container. Paper impregnated with the composite generates sufficient chlorine dioxide to protect the seeds. Although any seeds can be protected by the coating, edible seeds such as corn kernels, sunflower seeds, or soybeans, remain fit for human consumption once they are coated. Thus, the coated seeds can be provided for planting or for human consumption after they have been coated.

A composite of the present invention can also be formulated as a powder and admixed with soil to reduce microbiological contamination and fumigate the soil. If the powder contains nitrogen, phosphorus or some other elements, such as powders containing PGMS acid releasing wax or an amine hydrophilic material, it also fertilizes the soil.

The surface can be treated with any of the composites of the present invention by conventional coating, extrusion, lamination and impregnation methods well known in the art.

Another embodiment of the invention is a method of preventing the growth of fungi, bacteria or molds on a surface and/or deodorizing the surface by treating the surface with a composite that does not release chlorine dioxide in the absence of ambient moisture, and exposing the treated surface to moisture to release a gas such as chlorine dioxide from the composite into the atmosphere surrounding the surface.

A preferred application includes a foot powder for preventing athlete's foot and other fungi. The powder can be applied directly on the surface of the foot or can be incorporated into a shoe insert. The composite can be applied between the cloth covering and foam pad of the shoe insert, impregnated within the foamed pad, or impregnated or coated on a shoe counter or upper lining. Chlorine dioxide generated from moisture within the shoe diffuses from the composite into the atmosphere to kill fungus and deodorize the shoe. The powder can be blended with conventional ingredients such as talc, cornstarch, fragrance, miconazole nitrate, tolnastate silica, boric acid, aluminum chlorhydrate, salicylic acid, and cellulose. The powder can also be blended with other ingredients and used in bath powders or powders used in treating jock itch.

The powder can also be applied to carpeting to remove odors from the carpet. Ingredients commonly incorporated in powdered carpet deodorizers or cleaners can be blended with the powder of the present invention. The composite can also be formulated in microcapsules that break after being stepped on and are then activated by moisture. Such microcapsules can be impregnated in floor, shower or bath mats or can be used in carpet deodorization.

Another use for the composites is in providing self sterilizing packaging, which is particularly useful in the medical industry. A method of sterilizing a medical device, instrument or supply can be performed by applying a first composition to an outer surface of a first component, the first composition being inert in the absence of moisture; applying a second composition to an inner surface of a second component, the second composition being inert in the absence of moisture; contacting the first and second compositions on the surfaces of the first and second components to form a composite; and exposing the composite to moisture to initiate the release of chlorine dioxide from the composite into the atmosphere surrounding the medical device, instrument or supply to sterilize the medical device, instrument or supply. The first and second components can be interconnecting tubes. The composite can be coated onto tubing, connectors, fitments or other components as separate layers of the hydrophobic or hydrophilic material on separate components that are activated upon being pressure fitted together. Fitments for in-dwelling catheters, needles, peritoneal dialysis, percutaneous devices, percutaneous access, colostomy bags and other medical devices can also be treated in accordance with this method. Additionally, closures on a package can be so treated to provide self sterilizing packaging for medical devices, instruments and supplies.

The composite of the present invention was expected to kill bacteria on the surface of meats. However, it was not expected to penetrate a ground beef patty. It has been discovered that chlorine dioxide evolved from paper treated with the composite can effectively penetrate the full thickness of a patty and kill bacteria such as E. coli and Salmonella that result from contamination during meat processing. E. coli 0157:H7 in tainted meat has caused death and severe illness and appears to be especially resistant to cooking, fermenting and drying. In a typical operation producing meat patties for commercial consumption, meat is ground, extruded and formed into patties that are separated by sheets of coated paper that prevent adhesion of the individual patties. After packaging, the ground meat can be exposed to chlorine dioxide over a period of time when in refrigerated storage to kill and inhibit the growth of the bacteria.

A method of retarding, killing, preventing or controlling microbiological contamination on a surface of meat, poultry or seafood comprises exposing a surface of meat, poultry or seafood to a composite which does not release chlorine dioxide in the absence of moisture, and exposing the composite to moisture to release chlorine dioxide from the composite into the atmosphere surrounding the surface of the meat, poultry or seafood to reduce microbiological contamination on the surface and within the meat, poultry or seafood. The meat, poultry or seafood is preferably a ground patty or a filet. Microbiological contamination can be reduced on the surface and throughout a patty or filet. Preferably, microbiological contamination is reduced by at least about 50 fold or, more preferably, by at least about 99.5% on the surface and throughout a patty or filet. The composite can comprise a sheet for separating patties or filets during storage, the sheet being in contact with the surface of the meat, poultry or seafood. The composite can also be applied to a paper sheet for separating hamburger patties, a meat packaging tray, a food wrapper, a food container, or an absorbent pad.

Another method of retarding, killing, preventing or controlling microbiological contamination on a surface of meat, poultry or seafood comprises placing meat, poultry or seafood between sheets which do not release chlorine dioxide in the absence of moisture, and exposing the sheets to moisture to release chlorine dioxide from the sheets onto the meat, poultry or seafood to reduce the contamination on surfaces of and within the meat, poultry or seafood.

Another method of retarding, killing, preventing or controlling microbiological contamination in meat, poultry or seafood comprises exposing a surface of meat, poultry or seafood to chlorine dioxide gas for a period of time sufficient to reduce the contamination on the surface of and within the meat, poultry or seafood. Preferably, the surface of the meat, poultry or seafood is exposed to chlorine dioxide gas for at least about 60 hours.

The following examples are presented to describe preferred embodiments and utilities of the present invention and are not meant to limit the present invention unless otherwise stated in the claims appended hereto.

EXAMPLE 1

A hydrophilic material was made which contained a 7 wt. % solution of sodium chlorite in an amide mixture composed of 33 wt. % formamide, 33 wt. % acrylamide, and 33 wt. % isopropylacrylamide. A hydrophobic material consisting of a 40% solution of a copolymer composed of 33 mole % maleic anhydride and 66 mole % styrene in ethylbenzene plasticizer was then made. The hydrophobic material was vortex mixed with the hydrophilic material. The resultant white mixture of the two disperse materials started a sustained release of chlorine dioxide in the absence of added water within five minutes at room temperature. Interphase diffusion of water within the dispersion initiated hydrolysis of the anhydride. Hydronium ions formed during hydrolysis reacted with chlorite anions to release chlorine dioxide. The release rate could be slowed by cooling the mixture to 0° C. or by increasing the viscosity of the materials.

EXAMPLE 2

1-(N-dipropylamino)-2-carboxyamidoethane (DPACAE) was made by reacting 0.2 mole di(n-propyl)amine with 0.1 mole acrylamide in the presence of a small amount of acetic acid as a 10 wt. % solution in methanol. The reaction was carried out for 3 hours at 70° C. After vacuum evaporation of the excess amine and crystallization in the presence of pentane, a white low melting solid was obtained ($T_m$=60° C.) which tended to lose amine and form acrylamide upon prolonged heating above the melting point.

1-(N-Dimethylamino)-2-carboxyamidoethane (DMACAE) was made by reacting 0.2 mole dimethylamine (as a 40 wt. % solution in water) with 0.1 mole acrylamide as a 10 wt. % solution in methanol. The reaction was carried out for one hour at room temperature. After vacuum evaporation of excess amine, methanol and water, the DMACAE was taken up in methylene chloride, dried with magnesium sulfate and isolated as a low melting ($T_m$=45° C.) hydroscopic solid.

Both DPACAE and DMACAE crystallized only slowly and thus could be studied in the liquid state at room temperature. Neither neat liquid formed iminium chlorite. However, 10–30% wt. % solutions in formamide or acrylamideisopropyl acrylamide readily formed iminium chlorite when exposed to chlorine dioxide.

EXAMPLE 3

The amine-chlorine dioxide reaction was studied by layering the requisite amount of $6.0 \times 10^{-5}$ molar solution of chlorine dioxide in pentane onto about $3.0 \times 10^{-4}$ mole of amine, either in neat form or dissolved 10-30 wt. % in formamide or isopropyl acrylamide-acrylamide melt. The chlorine dioxide-pentane solution was prepared by reacting stoichiometric sodium chlorite with potassium persulfate in a small amount of water in the presence of pentane with vortex stirring in ice water. The supernatant pentane layer was then removed and kept dry in a sealed container over magnesium sulfate.

The formation of chlorite was detected by acidification of the reaction product and the observation of the odor and color of chlorine dioxide by UV/Vis spectroscopy after exposure to dilute HCl. In some cases the presence of chlorite was further verified by observation of the IR spectrum. Characteristic IR absorbance of chlorite at 830 cm$^{-1}$ verified its presence.

The following neat primary amines formed chlorite when exposed to chlorine dioxide:

$H_2NCH_2CH_2OCH_2CH_2OH$, $H_2NC(CH_3)_2CH_2OH$, $H_2NCH_2CH_2NHCH_2CH_2OH$, $H_2NCH(CH_3)_2$, $H_2NCH_2CH_2OH$,

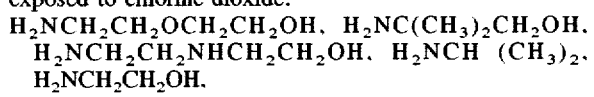

and

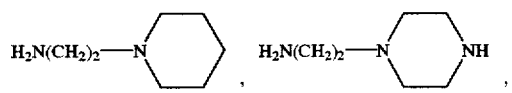

Chlorite was also formed by neat secondary amines having the formula $R_2R_3NH$ wherein $R_2$ and $R_3$ are, independently, hexyl, benzyl, n-propyl, isopropyl, cyclohexyl, acrylamide, or $-CH_2CH_2OH$. These amines also formed chlorite when the amine was in formamide solvent.

The following secondary amines yielded chlorite when plasticized with formamide or isopropylacrylamide-acrylamide:

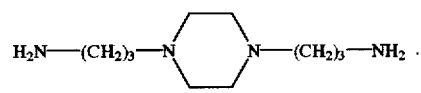

cyclohexyl or benzyl, and

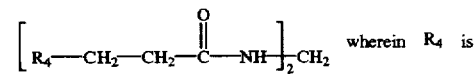

wherein n is 2 or 3.

The isopropylacrylamide-acrylamide and amine were also prepolymerized and film formed by heating to 60-70° C. in the presence of about 0.01% azobisisobutyronitrile initiator, providing chlorite so long as the film temperature exceeded the glass transition temperature.

A hydrogen bonded amine having the formula $R_8R_9NCH_2CH_2C(O)NH_2$ wherein $R_8$ is methyl and $R_9$ is n-propyl when in formamide or isopropylacrylamide-acrylamide solvent yielded chlorite. However, when $R_8$ and $R_9$ were isopropyl groups, the neat amine did not yield chlorite. A neat hydrogen bonded amine of the formula $N(CH_2CH_2OH)_3$ yielded chlorite, which was also formed when the amine was in formamide or isopropylacrylamide-acrylamide solvent.

To determine whether hydrogen bonding was necessary, a Michael addition process was used to provide a reaction product of 2-propenenitrile and $(i-C_3H_7)NHCH_2C_6H_5$ such that the amine portion of the product did not have any hydrogen bonding and the nitrile portion was very polar. Polarity was not sufficient to generate stable chlorite when the neat amine or the amine solvated in formamide was exposed to chlorine dioxide. The nitrile group blocked formamide so that the chlorite back attacked the amine and decomposed the chlorite into a form which could not be reconverted to chlorine dioxide. Thus, it was discovered that amines in apolar environments react with chlorine dioxide but the chlorite ion is unstable in such an environment.

Non-hydrogen bonded tertiary amines of the formula $NR_5R_6R_7$ wherein $R_5$ and $R_6$ are methyl and $R_7$ is cyclohexyl or 4-pyridyl were solubilized in formamide or isopropylacrylamide-acrylamide and formed a stable chlorite. Amines wherein $R_5$ is benzyl, $R_6$ is cyclohexyl and $R_7$ is dodecyl or wherein $R_5$, $R_6$ and $R_7$ are n-butyl or ethyl groups were insoluble in formamide and could not form any chlorite. $(CH_3)_2NCH_2CH_2N(CH_3)_2$ was soluble in formamide and yielded chlorite, but did not yield chlorite in isopropylacrylamide-acrylamide although it was solubilized by the solvent; the amine when neat or in acetonitrile did not yield chlorite.

Thus, it was discovered that an amine having a nitrogen of sufficiently high $pK_a$ solvated by a hydrophilic material or substituted by hydrogen bonding groups, such as hydroxylic, amide, primary amine or secondary amine substituents, forms chlorite by reaction with chlorine dioxide.

The amine-chlorine dioxide reaction as described above was repeated wherein the amine was dissolved in various solvents to determine the effect of the solvent on reaction efficiency. All chlorine dioxide was released in water. More chlorine dioxide was released in glycerin or ethylene glycol than was released in methanol, acetonitrile, methoxyethanol, ethanol or ethoxyethanol. Chlorite suspended or dissolved in a hydrophobic material, as a dilute solution in toluene or benzene, and exposed to chlorine dioxide reacted with chlorine dioxide but only released a minor amount of chlorine dioxide when acidified. Many of these solvents, such as ethanol, will not retain chlorite counterion for long term storage unless iminium chlorite is stabilized with a strong base to retain the chlorite counterion.

EXAMPLE 4

Amines that are monosubstituted with short apolar groups, such as $(CH_3)_2NCH_2CH_2C(O)NH_2$, $(n-C_3H_7)_2NCH_2CH_2C(O)NH_2$, and $(i-C_3H_7)_2NCH_2CH_2C(O)NH_2$, formed stable chlorite in formamide. Amines that were substituted with short apolar groups, namely $(CH_3)_2NCH_2CH_2C(O)NH(i-C_3H_7)$, $(n-C_3H_7)NCH_2CH_2C(O)NH(i-C_3H_7)$ and $i-C_3H_7N(CH_2CH_2C(O)NH_2)_2$, did not form stable chlorites. However, those with linear alkane lengths greater than or equal to six, such as $n-C_6H_{13}N(CH_2CH_2C(O)NH_2)_2$ and $n-C_{12}H_{25}N(CH_2CH_2C(O)NH_2)_2$, did form stable chlorite in formamide. It is possible that once the apolar chain length had achieved a certain length, a microphase separation into micelles with discreet hydrophobic regions surrounded by continuous hydrophilic regions took place. The destabilizing apolar phase was thus removed from the reaction environment.

EXAMPLE 5

The following polymers were synthesized, characterized using NMR techniques, and evaluated to determine physical properties and ability to uptake (and release) chlorine dioxide:

|—CH₂CH₂N (CH₂CH₂CH₃)—|ₙ
|—OCH₂CH(CH₂N(CH₃)₂)—|ₙ
|—CH₂CH(OCH₂CH₂N(CH₃)₂)—|ₙ
|—CH₂CH(C(O)N(H)CH₂CH₂CH₂N(CH₃)₂)—|ₙ

Of these polymers, the last polymer has the most flexible amine containing side group and exhibited the most efficient uptake and release of chlorine dioxide in formamide that is a substantial improvement over that demonstrated with in-chain amines. The polymer was also soluble in molten urea.

EXAMPLE 6

The following compounds containing an N-amido linkage and a tertiary amine center were synthesized in pure form from the corresponding primary or secondary aminef sodium cyanate, and hydrochloric acid as described by J. March, "Advances in Organic Chemistry: Reaction Mechanisms and Structure," 4th Ed., John Wiley, N.Y., p. 903 (1992).

Me₂N(CH₂)₃NHC(O)NH₂ HNMR: 1.5, 2.1, 2.2, 2.95, 5.5, 6.2

N(CH₂CH₂NHC(O)NH₂)₃ HNMR: 2.4, 3.0, 5.65, 6.25

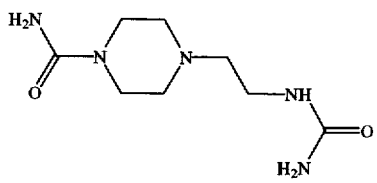

HNMR: 2.35, 3.2, 5.6, 6.05 ppm

Each of these compounds reacted with chlorine dioxide and later released it upon acidification in formamide, indicating that tertiary amine compounds with N-amido substitution of their primary and secondary amines can complex chlorine dioxide, when dissolved in a suitable hydrophilic solvent. Addition of urea to the formamide clearly improved the uptake and release efficiency.

EXAMPLE 7

Formation of Dimethylaminopropanamide

Acrylamide (3.05 g) was dissolved in methanol (31 ml) with stirring. The solution was cooled in an ice water bath for five minutes, and dimethylamine (1.94 g; 5.4 ml of 40 wt. % in water) was slowly added. The solution was cooled to room temperature and stirred overnight. Methanol and water were removed and a clear viscous liquid was recovered. The liquid was dissolved in dichloromethane (75 ml), dried over magnesium sulfate, filtered and the solvent was removed to yield a white solid. The solid was dissolved in ethyl ether (100 ml) and an insoluble, off-white residue having a decomposition temperature of 150° C. was recovered. The filtrate was treated with hexane and crystallization started at once. The solvent was removed and the remaining crystals were washed with hexane (30 ml) which was then removed. The dried crystals had a melting point of 40–41° C. IR and NMR spectra agreed with the chemical structure for 3-dimethylaminopropanamide (DMAP). The chemical structure is further confirmed because the reaction is a Michael addition. The acrylamide is a Michael-type substrate CH₂=CHZ wherein Z is —C(O)NH₂. The nitrogen of the dimethylamine (CH₃)₂N bonds to the carbon of acrylamide that does not carry the Z radical, as evidenced by the discussion of hydro-amino addition in J. March, *Advanced Organic Chemistry*, 4th Ed., (John Wiley & Sons, N.Y., N.Y.), p. 768.

Formation of Hydrophilic Materials

Up to 50 wt. % of the tertiary amine DMAP was added to hydrophilic solvent containing 50 wt. % urea and 50 wt. % n-methylacetamide (NMA) solvent at 50° C. and quickly cooled to room temperature. The solution remained single phase indefinitely at room temperature. The same behavior was noted for the addition of 20 wt. % DMAP to a solvent containing 33 wt. % urea, 33 wt. % NMA and 33 wt. % sodium acetate, a solvent containing 35 wt. % urea, 55 wt. % NMA and 10 wt. % sodium methoxide, and a solvent containing 70 wt. % urea and 30 wt. % sodium acetate.

Exposure of Hydrophilic Materials to Chlorine Dioxide

The above mixtures were exposed to a solution of chlorine dioxide in pentane and were observed to rapidly uptake (one minute) one chlorine dioxide for every two amine groups before the reaction slowed substantially. The final pH of the hydrophilic material remained on the basic side. A slight cloudiness was seen in the 50 wt. % urea/50 wt. % NMA—DMAP mixture and the 33 wt. % urea/33 wt. % NMA/33 wt. % sodium acetate—DMAP mixture while the DMAP—35 wt. % urea/55 wt. % NMA/10 wt. % sodium methoxide mixtures remained clear.

A representative example of the reactions that occur when a hydrophilic material containing a base is exposed to chlorine dioxide gas is as follows. When a hydrophilic material including DMAP in a urea/NMA/sodium methoxide solvent is exposed to chlorine dioxide, DMAP reacts with chlorine dioxide to form an aminium chlorite that reacts with chlorine dioxide to form an iminium chlorite as shown below:

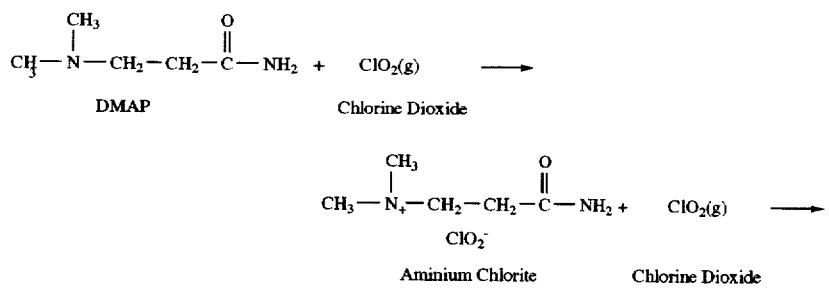

-continued

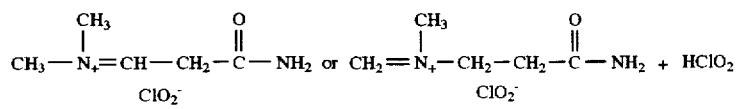

Iminium Chlorite

The sodium methoxide reacts with the iminium chlorite to form an α-amino ether and sodium chlorite as follows:

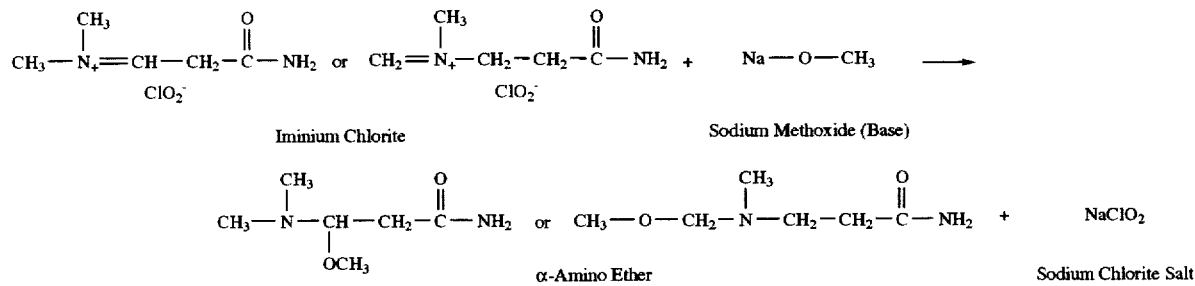

Acidification of Hydrophilic Materials to Generate Chlorine Dioxide Release

Upon acidification by 0.1N HCl (pH<5), complete release of chlorine dioxide from all three mixtures was observed up to 30 minutes after formation of the chlorite salt. The release of chlorine dioxide was estimated by referring to the color of solutions containing known amounts of chlorine dioxide. After this time different behavior was observed. For example, after two hours, the 50 wt. % urea/50 wt. % NMA—DMAP mixture released no chlorine dioxide. The 33 wt. % urea/33 wt. % NMA/33 wt. % sodium acetate completely released chlorine dioxide after two hours at room temperature. However, only one third of the chlorine dioxide was released after 24 hours at 5° C., with no chlorine dioxide being yielded after an additional 24 hours at room temperature.

35 wt. % urea/55 wt. % NMA/10 wt. % sodium methoxide exhibited the greatest chlorite salt stability in that complete release was noted after three days storage at 5° C. Complete release was also noticed after 24 hours at room temperature. The presence of a strong inorganic base greatly improves the stability of the chlorite salt in urea based solvents.

Decomposition Testing of Hydrophilic Material

A 20% DMAP—35 wt. % urea/55 wt. % NMA/10 wt. % sodium methoxide melt was examined at 60° C. for up to one hour in 300 MHz proton NMR to see if any DMAP decomposition occurred. From the toxicological point of view any decomposition of the DMAP into secondary amine and toxic acrylamide would be highly undesirable.

No decomposition was observed over the one hour heating period. Acrylamide alkene resonances were expected between 6–4 ppm yet none were seen. Some polymerization of the urea was revealed by the broad band under a sharp urea band at 6–7 ppm. The NMR obtained after heating at 120° C. for two hours, much above the 50° C. at which the DMAP was mixed into the urea based solvent, revealed extensive polymerization of the urea that was evident from the increase in line width and the complication in the urea resonance between 8 and 6 ppm. However, no alkene acrylamide resonances were seen. Thus, the 20% DMAP—35 wt. % urea/55 wt. % NMA/10 wt. % sodium methoxide system produced no toxic alkene products.

Formation of Hydrophilic Materials Forming an α-Amino Ether and Chlorite Salt in Situ Upon Exposure to Chlorine Dioxide Gas and Acidification To avoid variability in chlorite stability from incomplete drying of the solvent, 40 wt. % of carefully dried urea (vacuum dried: 80° C., 18 hours, 0.1 torr) and 60 wt. % NMA (CaO overnight reflux and distilled) were mixed and heated for 18 hours at 120° C. Alkoxides were first isolated as dry powders by reacting the required amount of clean sodium metal with the alcohol and isolating the product by washing with diethyl ether. All mixing was carried out under dry nitrogen atmosphere. Predrying of the urea/NMA mixture resulted in room temperature stability of the iminium chlorite salts for at least one week at room temperature.

The desired amount of alkoxide was then dissolved in the urea/NMA solvent using minimal heating followed by DMAP to form a clear viscous liquid at room temperature. The hydrophilic material was then exposed to chlorine dioxide gas and acidified as described above.

Table 1 indicates the improved chlorine dioxide release characteristics of several urea/NMA/DMAP/sodium alkoxide hydrophilic materials after they are acidified. Release characteristics are based on a relative scale ranging from excellent (9) to poor (1).

TABLE 1

| | Sodium Alkoxide[a] | % Alkoxide | % Amine[b] | Equiv. ClO$_2$[c] | Day 0 | Day 1 | Day 2 | Day 3 | Day 4 | Day 5 | Day 6 | Day 7 |
|---|---|---|---|---|---|---|---|---|---|---|---|---|
| A | — | 0 | 30–50 | 0.5 | 9 | 0 | 0 | 0 | 0 | 0 | 0 | 0 |
| B | C1 | 7 | 20 | 0.5 | 9 | 4 | 0 | 0 | 0 | 0 | 0 | 0 |
| C | C1[d] | 15 | 20 | 0.5 | 9 | 4 | 0 | 0 | 0 | 0 | 0 | 0 |
| D | C2 | 23 | 20 | 0.5 | 9 | 8 | 7 | 7 | 7 | 6 | 6 | 5 |
| E | C2 | 30 | 22 | 0.75 | 3 | 2 | 1 | 1 | 1 | 1 | 1 | 1 |
| F | i-C3 | 20 | 20 | 0.5 | 9 | 8 | 7 | 6 | 5 | 5 | 3 | 3 |
| G | i-C3 | 31 | 27 | 0.5 | 9 | 9 | 8 | 8 | 7 | 7 | 6 | 5 |
| H | t-C4 | 16 | 30 | 0.5 | 9 | 8 | 7 | 4 | 4 | 2 | 2 | 1 |
| I | t-C4 | 30 | 23 | 0.5 | 9 | 9 | 8 | 8 | 7 | 7 | 6 | 6 |
| J | NaClO$_2$ | 7 | — | — | 9 | 9 | 9 | 9 | 9 | 9 | 9 | 9 |

[a]Methyl and t-butyl alkoxides are commercial products.
[b]Percentages are based on material already present in the mixture at that stage and not the final composite.
[c]Based on amine
[d]These experiments were done without predrying of the urea and NMA.

Hydrophilic materials B–I exhibited a period of sustained chlorine dioxide release as compared to hydrophilic material A which did not include a base. Hydrophilic materials B and C containing sodium methoxide released chlorine dioxide for about 24 hours. Hydrophilic materials D, G and I containing sodium ethoxide, sodium isopropoxide or sodium t-butoxide, respectively, released at least 60% of the chlorine dioxide after three weeks storage in dry, dark conditions. Since no change in the chlorine dioxide release was noted after one week, these hydrophilic materials were considered indefinitely stable after one week. The hydrophilic material A released chlorine dioxide for a period of hours but did not release chlorine dioxide after that time, as shown by a 0 release rate for days 1–7. Thus, the hydrophilic materials containing an amine exhibited long term chlorite stability when stabilized by a base. However, the addition of more than 0.5 mole chlorine dioxide per mole of amine substantially decreased iminium chlorite stability.

When the hydrophilic material is part of a composite of the invention, the hydrophobic material will provide the acid for initiating chlorine dioxide release rather than acidifying the material with HCl as described above.

EXAMPLE 8

In order to make a hydrophobic acid releasing wax, hydrocarbon wax ($T_m$=60° C.) or atactic polypropylene (APP) was first melted at 70° C. under nitrogen with stirring. An equivalent weight of glycerol monostearate or glycerol distearate was then dissolved in the molten wax or APP. Two equivalents (based upon phosphorous) of powdered phosphorous pentoxide per three equivalents of glycerol compound hydroxyl functions was slowly added to the melt to avoid clumping. After stirring the melt an additional two hours at 80° C., one equivalent of tetraethylorthosilicate was added and the immediate evolution of ethanol was detected. Stirring was continued for an additional four hours while slowly raising the temperature to 100° C. and purging the mixture of ethanol with a 10 cc/minutes flow of nitrogen. The reaction flask was subsequently evacuated at 100° C. to remove any remaining ethanol or tetraethoxysilicate, filled with nitrogen and cooled. Softening of the wax-acid releasing agent (LPOSI) started at about 60–70° C. The viscosity of the wax was 100 cP at 100° C.

The process for preparing LOPSI can be summarized as follows. When hydrolyzed, silicon dioxide and a phospholipid are formed.

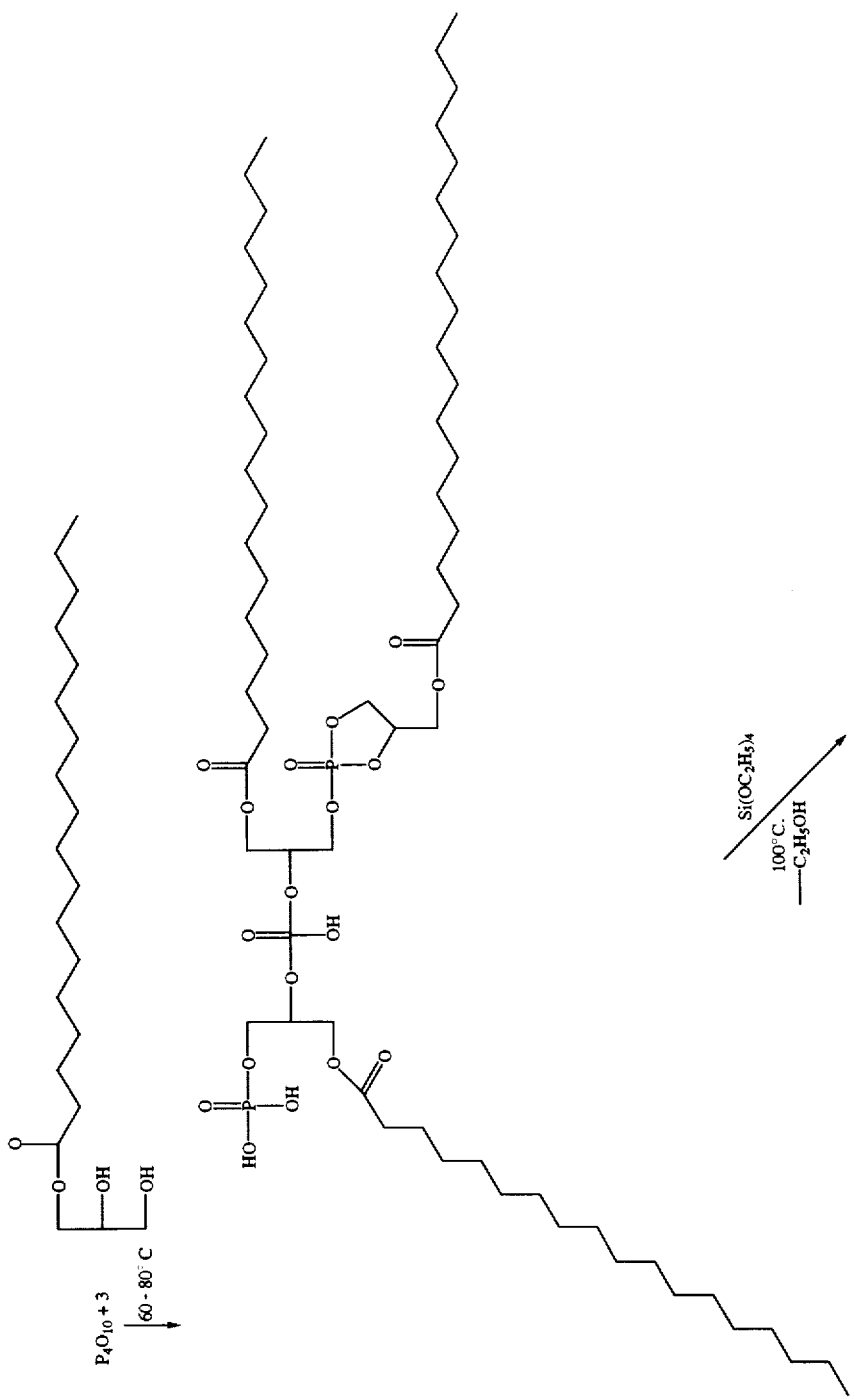

-continued
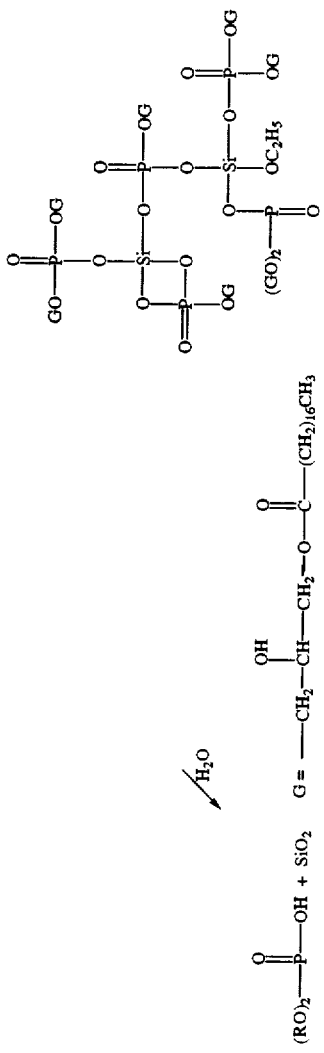

Chlorite powder was prepared by first dissolving commercial sodium chlorite in dry methanol at 3% by weight and filtering the resultant solution to remove sodium carbonate impurity. The chlorite solution was then extruded into an anhydro spray drier in dry nitrogen at 100° C. through a self siphoning extrusion head with co-axial fluid and nitrogen flow. After routing to a cyclone separator to isolate small sodium chlorite particles of about 5 microns in diameter, the powder was stored in a dry atmosphere.

Neat sodium chlorite powder or mixtures of sodium chlorite powder and anhydrous sodium sulfate in a ratio of 1:1 and 1:2 by weight was fluidized in the bottom of a nitrogen filled container. A stream of acid releasing wax was then directed into the fluidized bed through a nozzle of 7 mil in diameter with a nitrogen back pressure of 30–80 lbs/in$^2$ to produce wax particles encapsulated with chlorite and sulfate particles (indicated as 1:1 pre and 2:1 pre in FIG. 4). The freely flowing powders were then stored in a dry atmosphere. In some cases anhydrous sodium sulfate was post-mixed with the chlorite-wax particles (i.e., 1:1 post and 2:1 post in FIG. 4).

FIG. 4 shows the chlorine dioxide release rate from 200 mg of several powder composites placed in a Petri dish of approximately 62 cc volume with a leakage of $2 \times 10^{-9}$ moles/sec. Controlled release over several days is accomplished at about 75° F. and 40% relative humidity.

EXAMPLE 9

A hydrophobic acid releasing wax was made as described in Example 8. The controlled release layer for an immediate release system was formulated by melt coating approximately 5 mil of acid releasing wax in a low melting hydrocarbon wax (60° C.=$T_m$) onto both sides of a piece of paperboard. Next, approximately a 5 mil thick layer of 10% by weight, methanol recrystallized, sodium chlorite in the low melting wax was melt coated onto the acid releasing layer. Another acid releasing layer of about 5 mil thickness was then coated onto the chlorite containing layer. The total volume of controlled release material was 0.25 cc.

Two chlorine dioxide measuring sensors (0–10 ppm and 0–100 ppm) were interfaced with a computer so that chlorine dioxide concentration was recorded as a function of time over a two week period automatically along with humidity and temperature. Both sensor ends were exposed to the chlorine dioxide atmosphere in a closed Petri dish through two small holes drilled into the top cover of the Petri dish. The humidity and temperature in the room were close to that measured in the Petri dish because the Petri dishes were of the "breathable" type where the cover made contact with the base at a serrated edge and no effort was made to insulate the Petri dish from its surroundings.

Figure 5:
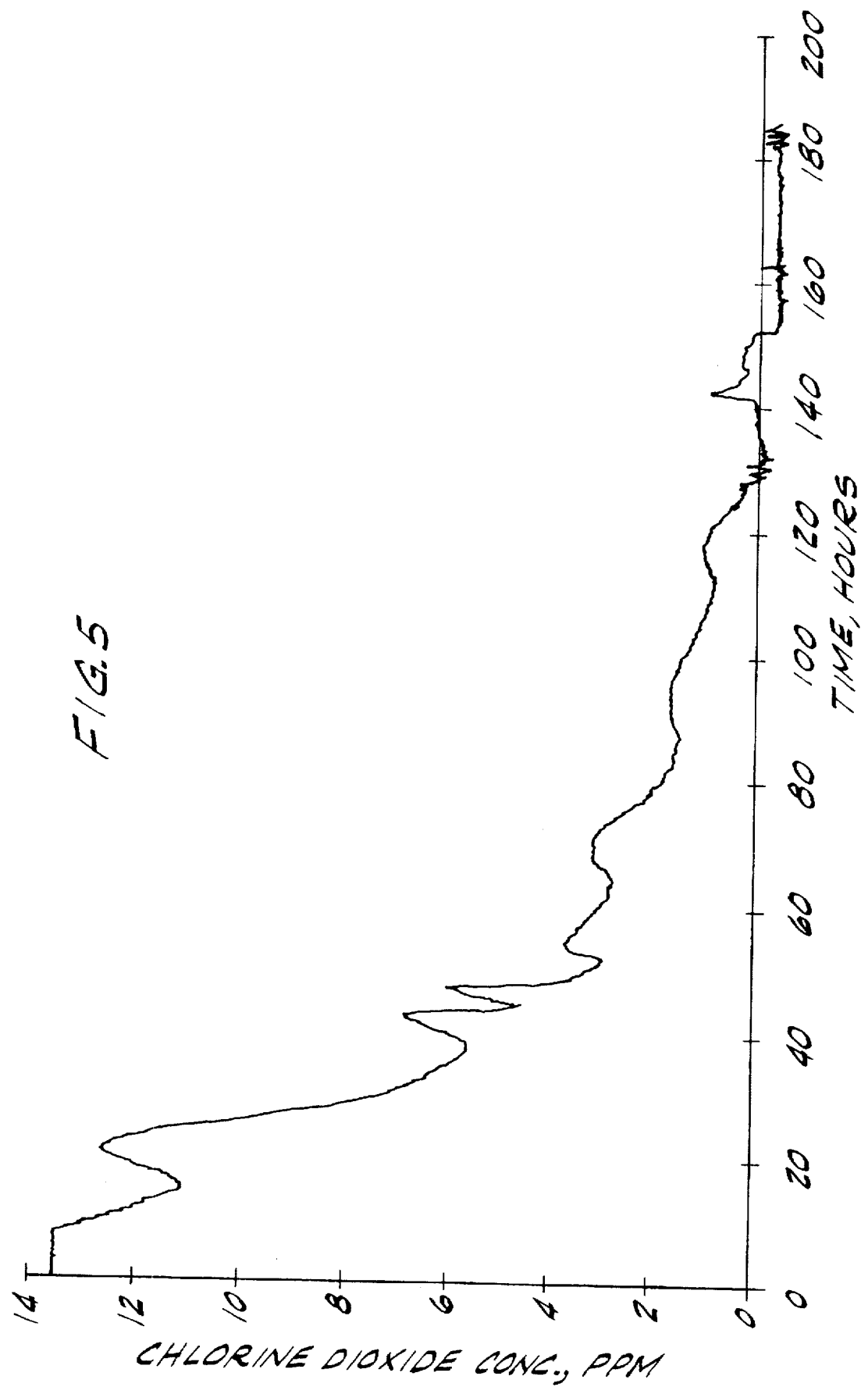
FIG. 5 is a plot of chlorine dioxide release rates for a layered composite.
Figure 6:
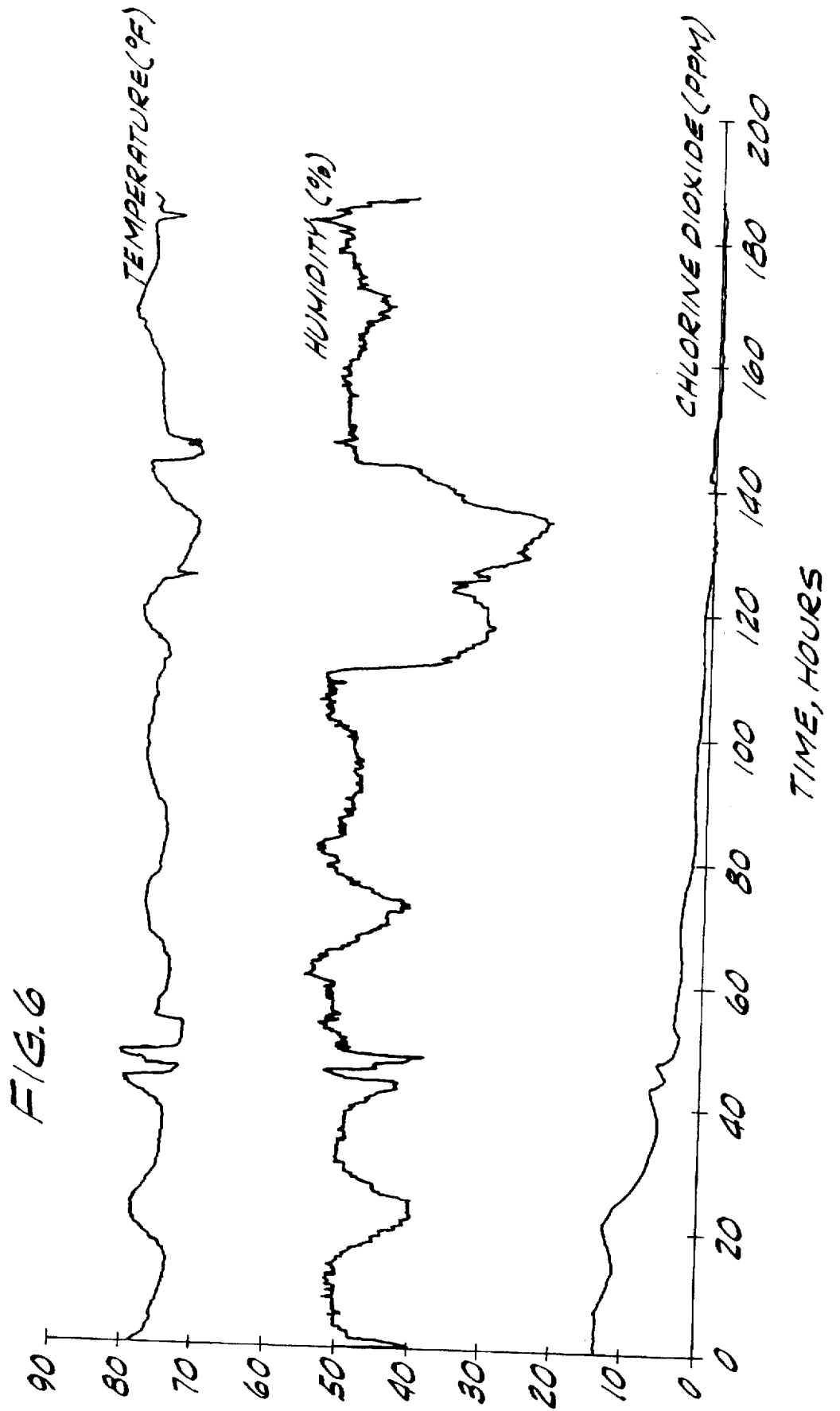
FIG. 6 is a plot of chlorine dioxide release rates in relation to atmospheric temperature and humidity.

In this configuration, the acid releasing layer was placed in direct contact with the chlorite containing phase and immediate release of chlorine dioxide was observed as soon as the film was placed in the Petri dish. The chlorine dioxide gas concentration dropped from a high of 13 ppm to 1 ppm at 5–6 days in an exponential fashion as shown in FIG. 5 (note that detector error of ±0.5–1.0 ppm resulted in less than zero concentration). However, surprisingly, the concentration peaks that were superimposed upon this exponential behavior, were correlated with the temperature and not the relative humidity as shown in FIG. 6.

Three mold species, *Chaetomium globosum* (CG), *Aspergillus terreus* (AT), and *Aspergillus niger* (AN), were grown in mineral loaded, but nutrient free agar slants using paperboard as a nutrient. All growth studies were carried out in accord with TAPPI standard method T 487 pm-85 entitled "Fungus Resistance of Paper and Paperboard."

Six samples were tested for fungus resistance over two weeks at room temperature in duplicate. Photographic comparisons showed considerable growth after two weeks on the control samples, while no growth showed on the controlled release films. The effectiveness of chlorine dioxide in killing these three molds was evident from the two week study.

EXAMPLE 10

In a delayed release system one side of a piece of paperboard was coated with an acid releasing layer separated from a chlorite layer by an intermediate wax layer. The 5 mil thick hydrophilic phase in the chlorite layer was a transparent blend containing 10 wt. % sodium chlorite, 50 wt. % $(NH_2C(O)CH_2CH_2OCH_2CH_2)_2O$ and 40 wt. % formamide. The chlorite layer was separated from the acid releasing LPOSI wax of about 5 mil thickness by an unmodified wax layer of about 5 mil thickness. The total volume of controlled release material was about 0.25 cc.

Figure 7:
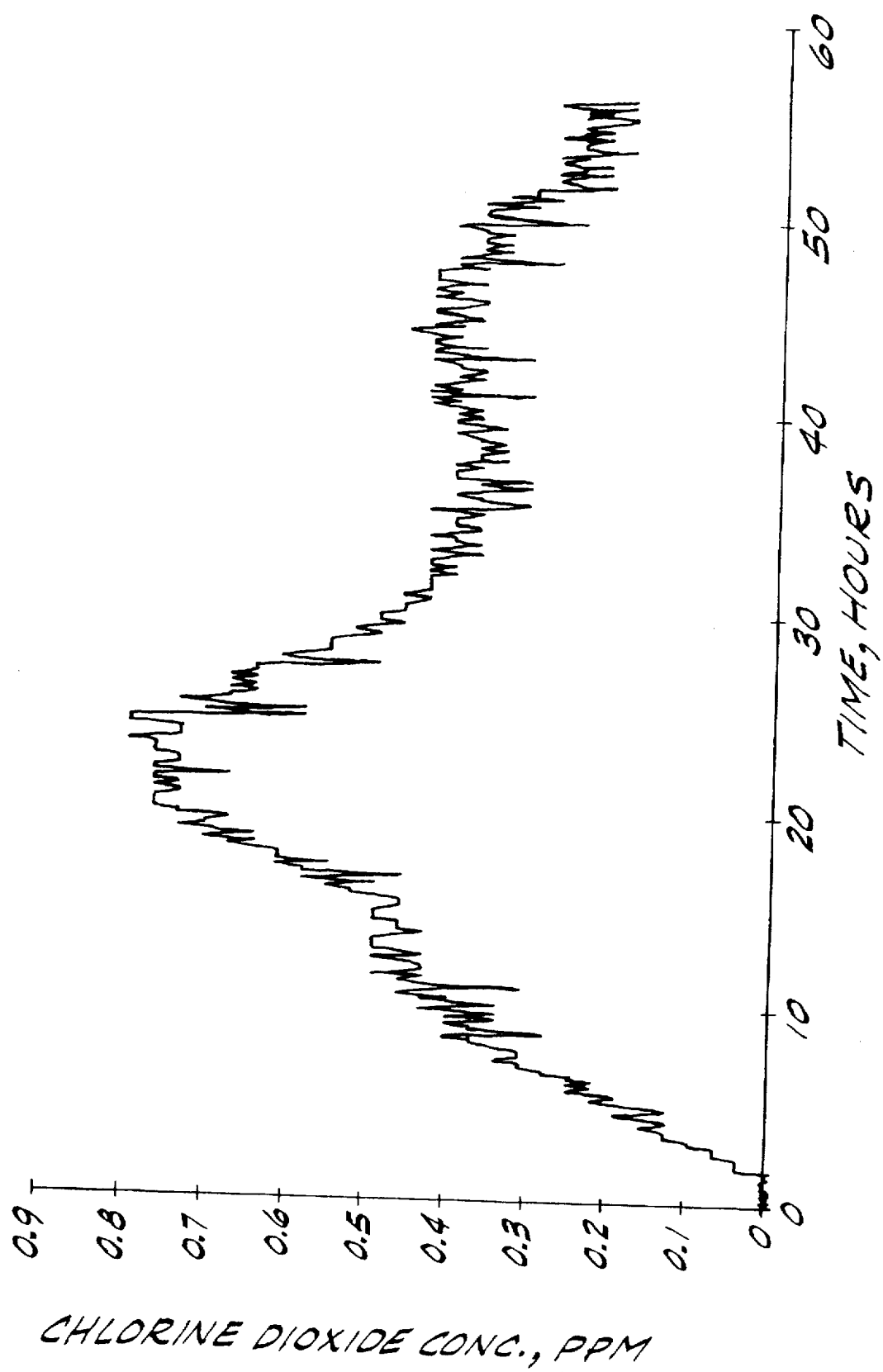
FIG. 7 is a plot of chlorine dioxide release rates for a layered composite.
Figure 8:
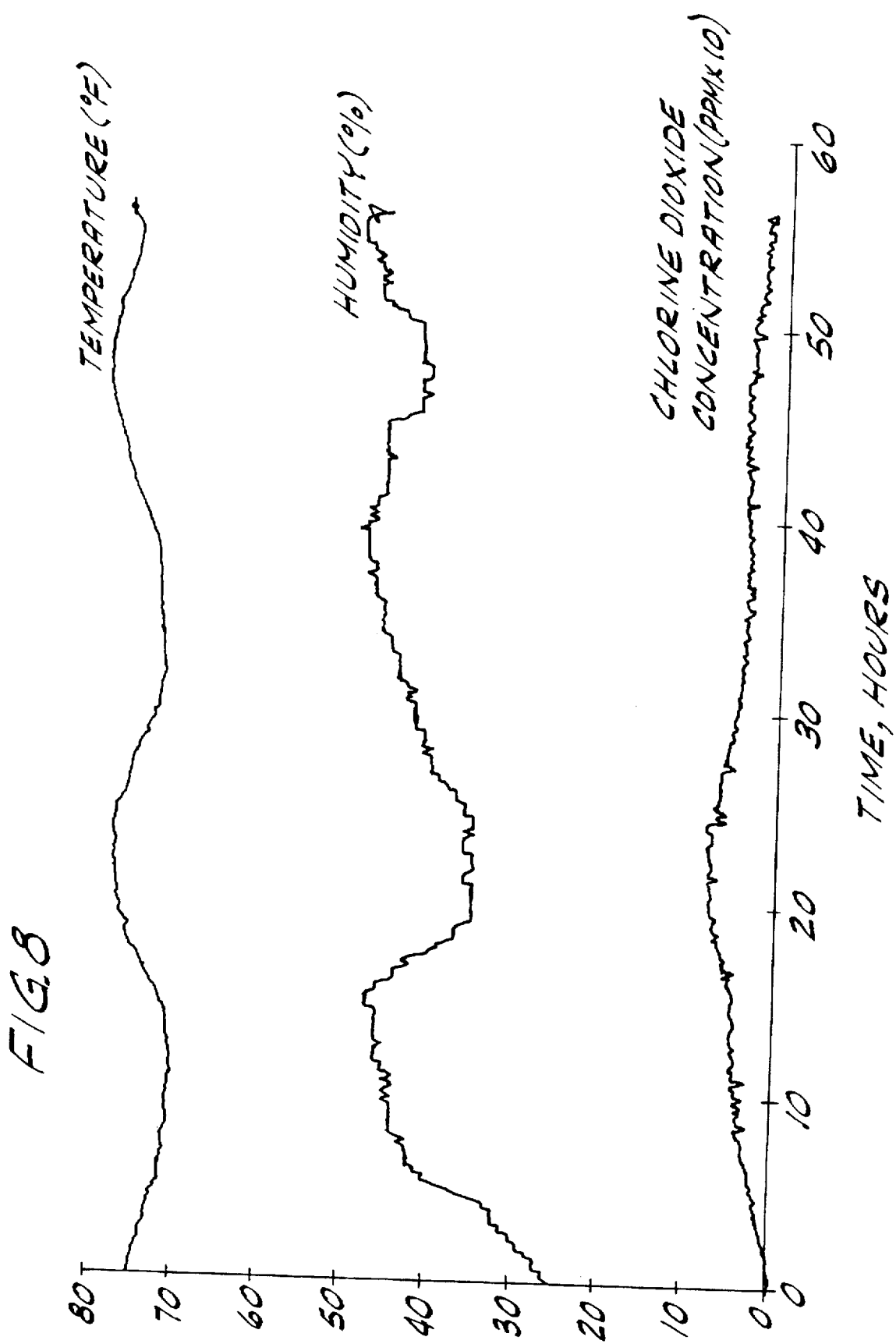
FIGS. 8 and 9 are plots of chlorine dioxide release rates in relation to atmospheric temperature and humidity.

A delay in chlorine dioxide release was noted when the acid releasing layer was separated from the chlorite containing layer by an intervening wax layer. In this case, a peak in the release was noted after one day as shown in FIG. 7. Individual concentration peaks superimposed on the averaged behavior were again correlated with the temperature and not with the humidity as shown in FIG. 8.

The three mold species tested for in Example 9 were grown in mineral loaded, but nutrient free agar slants using paperboard as a nutrient in accord with TAPPI standard method T 487 pm-85.

Six samples were tested for fungus resistance over two weeks at room temperature in duplicate. The results are presented in Table 2. Photographic comparisons showed considerable growth after two weeks on the control samples, while most of the controlled release films showed no growth. In the few cases where mold did grow on the controlled release films, only a single nucleus was responsible. Invariably, this nucleus was a large clump of mold spores where some self protective effect was generated by the aggregate structure.

TABLE 2

|  | CG Mold | AT Mold | AN Mold |
|---|---|---|---|
| Control Lawns[1] | Growth<br>Growth from single mold spore | Growth<br>No growth | Growth<br>No growth |
| Soak[2] | Growth from single mold spore | No growth | Growth from single mold spore (trial 1), No growth (trial 2) |

[1]Agar covered with mold spores
[2]Paper soaked in mold spores

EXAMPLE 11

The porous paper used throughout these examples had one untreated side and one side which appeared glossy. The chlorine dioxide release coatings were applied to the untreated side of the paper with the chlorine dioxide releasing composite sheets assembled with the glossy side out. Consequently, only the glossy side of the paper had contact with the meat. Sheets approximately 3 ft.×8 in. were cut to facilitate handling during the coating process. The original paper weight was 5 mg/cm$^2$.

LPOSI acid releasing wax was applied to the porous substrate paper in a nitrogen filled dry box containing a large dish of stirred phosphorus pentoxide using a wax coater operating at approximately 190° F. If multiple coatings were used, the paper was allowed to cool prior to applying subsequent layers. Once the paper was coated, it was sealed in a dry atmosphere suitable for storage.

The chlorite containing paper was applied from methanol solution using a coater operating at room temperature. A typical coating solution was prepared by first dissolving 25 grams of poly N-vinyl pyrrolidinone (PVNP, $1.7 \times 10^6$ M.W.) in 500 ml of methanol followed by 15 grams of sodium chlorite (technical grade). The homogeneous solution was used immediately. If multiple coatings were desired on a single substrate, the coating was allowed to dry between applications. The chlorite containing paper was then sealed in dry atmosphere for storage.

Immediately prior to use, the chlorite containing film was compression molded at room temperature with the LPOSI containing film to form a chlorine dioxide releasing bilayer composite. Pressures under 10,000 lbs/in$^2$ were sufficient to induce cold flow and adhesion of the wax to the chlorite containing film.

Samples of each individual sheet of coated substrate bilayer were randomly set aside during the pressing operation in order to quantify the chlorite and wax loadings. These sheets were cut, measured and weighed, then compared with data obtained from uncoated paper as shown in Table 3. Calculations of the theoretical acid output based on phosphorous pentoxide and the relation:

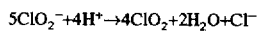

indicate a ratio of approximately 0.14 g NaClO$_2$/g wax for optimum ClO$_2$ utilization.

TABLE 3

| Sample (ClO$_2$:Wax) | # ClO$_2$/PVP coatings | NaClO$_2$ (mg/cm$^2$) | # Wax coatings | Wax (mg/cm$^2$) | $\frac{g\ NaClO_2}{g\ Wax}$ |
| --- | --- | --- | --- | --- | --- |
| 1:1 | 1 | 0.44 | 1 | 2.9 | 0.15 |
| 3:6 | 6 | 1.6 | 3 | 6.3 | 0.25 |
| 2:4 | 4 | 1 | 2 | 5 | 0.21 |
| 2:2 | 2 | 0.45 | 2 | 4.7 | 0.096 |

Figure 9:
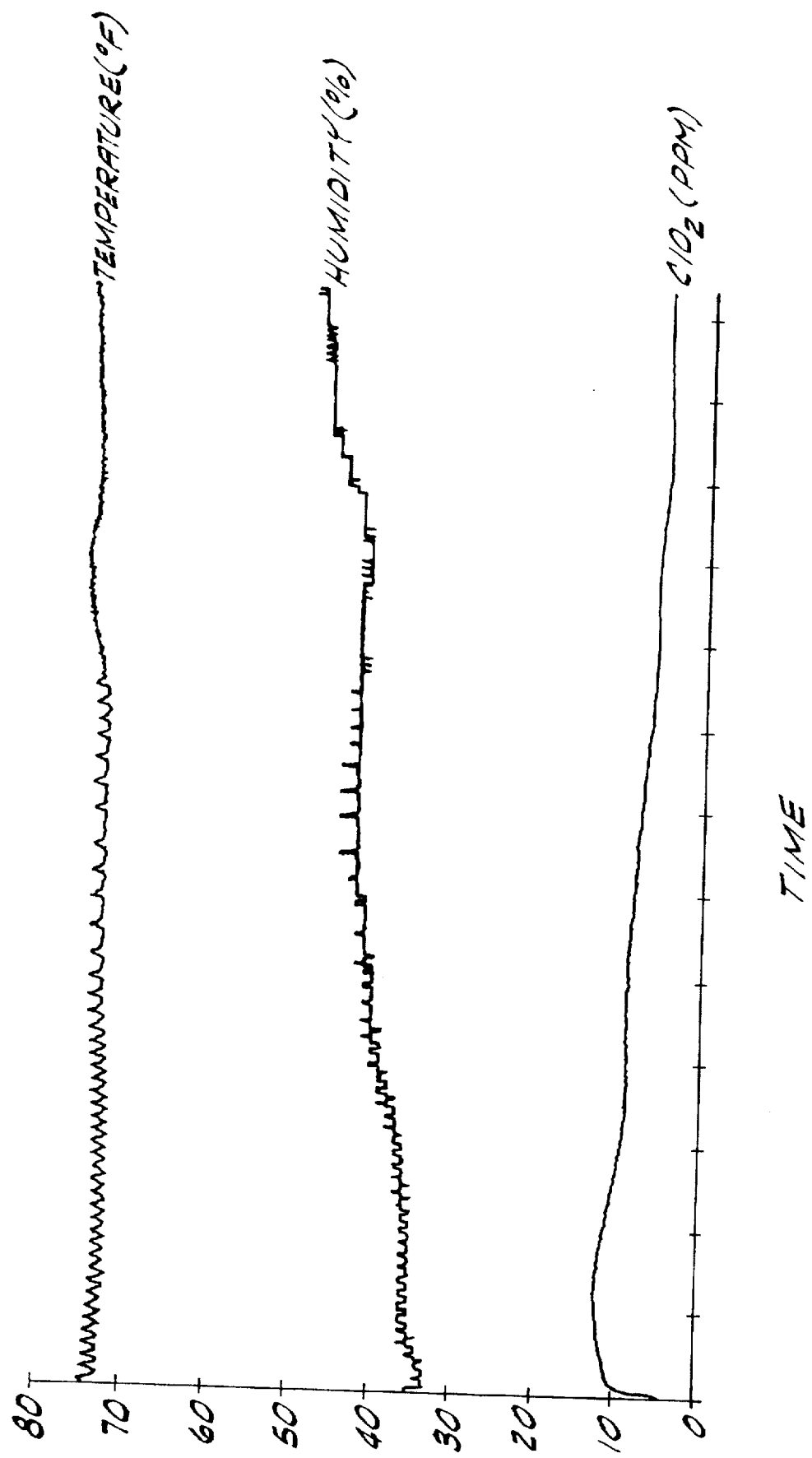

The chlorine dioxide concentration released from the films along with humidity and temperature was monitored in a Petri dish under atmospheric conditions using the sensor system and gas leakage rate previously described in Example 9. Samples were monitored over several days. FIG. 9 shows a typical plot generated from data acquired from a sample composed of sheets with two coats of each phase (2:2). Samples were monitored at several different loading levels. All samples showed an immediate maximum release of 10–20 ppm chlorine dioxide within the first 2–3 hours followed by a very gradual reduction in release over the next several days. Higher loadings served to increase the maximum initial concentration and prolong the release.

EXAMPLE 12

2:2 loaded papers were used as separators between ground meat patties packed to different densities that were loaded initially with high loadings of colony forming units (CFU) of *E. coli* bacteria. Substantial reductions in bacterial growth were noted as shown in Table 4. In loosely packed patties, the chlorine dioxide gas had access to the interior of the patty, resulting in a more complete kill throughout.

TABLE 4

| Ground Meat | Bacterial Load (CFU/patty) | % Reduction in *E. coli* bacteria |
| --- | --- | --- |
| Loosely packed | $1.7 \times 10^7$ | >99.99% |
| Densely packed | $5.0 \times 10^7$ | 99.5% |

EXAMPLE 13

*Escherichia coli* ATCC (American Type Culture Collection) #26 was grown in Tryptic Soy Broth (Difco 0370-17-3) to a log phase activity with an optical density of 0.8 at 600 nm containing one billion colony forming units per ml of culture. The concentration was verified using plate counts on three separate dilutions.

Uniform dispersal of the bacteria was assured in densely packed meat by the following inoculation method. Chili-ground sirloin purchased six hours before use and stored at 8° C. weighing two kilograms was placed in a pan and pressed down into an even sheet. Five holes were punched into the meat with a glass rod, and 0.1 ml of the bacterial culture was pipetted into each hole. The meat was then kneaded to disperse the bacteria evenly. This was repeated three more times, with at least a minute of vigorous kneading each time. Since the two ml of an inoculum with a culture concentration of 10$^9$ cfu per ml was added to the meat, a concentration of one million cfu/gram was introduced into the meat.

The meat was then reground to a fine texture on a bench-mounted, hand-cranked sausage grinder and formed into patties by replacing the meat in the pan and cutting patties out with a piece of tubing to form positive control (i.e., added *E. coli* bacteria) patties. The negative control (i.e., no added bacteria) ground sirloin from the same source was ground first in the uncontaminated grinder to prevent its own contamination. The patties were prepared in duplicate and consisted of negative controls tested at 0 and 60 hours, positive controls tested at 0, 4, 24 and 60 hours, and test samples (i.e., patties exposed to a chlorine dioxide releasing film of the present invention) at 0, 4, 24 and 60 hours.

The patties were placed between either unmodified paper or the papers coated with a 2:2 chlorine dioxide releasing film (as described in Example 11) in 10 cm diameter plastic Petri dishes with covers. Two Petri dishes containing duplicate samples were then put in recloseable plastic bags and stored for the required time at 4° C. in a common refrigerator.

Two samples were taken from each patty, one from the upper surface, T, contacted either by the unmodified paper or by the test paper with the chlorine dioxide releasing film, or from the middle one third of the patty, M. Samples were obtained with angle tipped forceps by either pinching across the surface to obtain a small scraping of the meat, or by digging down and exposing the middle third thickness region. The forceps were sterilized between samples by dipping in isopropanol and flaming.

Ten ml sterile water blanks in screw capped test tubes were tared to zero on a sensitive electronic scale, and roughly one gram samples added to the tubes and the weights recorded. The tubes were then capped and shaken vigorously to disperse the meat and release the bacteria.

0.1 ml of the supernatant was plated onto Tryptic Soy Agar (Difco 0369-17-6) in duplicate and spread with a glass triangle on a turntable. The glass spreader was sterilized between platings with isopropanol and flamed. The viable bacterial content of the samples was visualized by inverting the plates after 24 hours incubation at 37° C.

Uninoculated negative controls showed the normal amount of bacteria commonly seen in ground sirloin with no substantial growth noted over 60 hours at 4° C. Inoculated positive controls showed large amounts of bacterial growth for all times with very minor differences between the top and middle samples. If the unmodified paper had an antimicrobial effect, it was minor.

When the colony counts of chlorine dioxide exposed test samples were compared, a 50-100X kill was noted for the surface sample as compared to the interior test sample and the positive control samples, except for the reduced surface kill on the sample contacted with the weakly releasing film. As for the four hour exposed test samples, surface colony growth was 50-100X less than the interior test sample or the positive controls. The surprising observation made on the 60 hour sample was the high kill in both the interior and surface sections of the exposed samples when compared to the positive control samples.

Because the positive control plates were expected to be overloaded, a direct comparison for quantitation purposes was not accurate, although a rough count revealed anywhere between 50-200 fold reduction in colony count. As an alternative the test plate counts were compared to the confirmed inoculum titer instead.

A rough comparison may be made between the Ccfu and the inoculum figure (corrected for sampling dilution). This is termed the ratio to inoculum (RTI), which is intended to compare the viability of the treated sample and the maximum possible cfu count. RTI's were calculated for the 60 hour plates on the basis of the Ccfu count.

The average RTI for the top samples of the plates for the patties that were exposed to chlorine dioxide and tested for 60 hours was roughly 170, which would represent a 170 fold decrease in viability. The average RTI for the interior of these patties was roughly 50.

At 60 hours, however, large reductions in the bacterial viability in the center of the patty were seen. Cooking the patties that were exposed to chlorine dioxide and tested for 60 hours yielded a normal looking hamburger with no unusual odors being noted.

EXAMPLE 14

Loosely packed 0.75 inch thick, ground sirloin patties with approximately 25 cm² top surface area were formed by hand immediately after mixing and grinding in of $E.\ coli$ ATCC #26 broth ($10^5$–$10^6$ cfu/gram). The initial inoculum was grown up to a slightly lesser extent than the inoculum used in Example 13. The loose packing was employed to help the penetration of chlorine dioxide through interconnected air passages.

The patties then were placed between either 2:4 or 3:6 chlorine dioxide releasing papers as described in Example 11, and covered with a Petri dish cover which was enclosed in a recloseable plastic bag. The samples were then stored at 4° C. for 3.5 days. After this exposure time the meat in contact with the 3:6 papers showed no bacterial growth from either a surface or interior sample when plated as described in Example 13. The interior of the patty exposed to the lower chlorine dioxide concentration (2:4) showed no bacterial growth from either surface or middle samples when plated.

When compared to the results of Example 13, these results confirm the deep penetrating biocidal action of chlorine dioxide when released in a controlled fashion over 2.5–3 days at 4° C. Clearly, the biocidal action is more effective for a porous meat structure.

An additional experiment using chicken breasts was also performed. A filet of chicken breast was repeatedly dipped in undiluted $E.\ coli$ ATCC #6 broth ($10^8$–$10^9$ cfu/ml), placed between 2:2 chlorine dioxide releasing films and then closed inside a Petri dish which was placed in a recloseable plastic bag and placed in a refrigerator at 4° C. for 3.5 days. The surface of the meat was then swabbed and plated to get an indication of bacteria kill. Again no bacterial growth was noted after incubation.

EXAMPLE 15

Design of a chlorine dioxide releasing film suitable for controlled release and biocidal action within a container is described herein. The equation describing the concentration of chlorine dioxide in a coating of thickness, 1, ($0<x<l$) which is covering the inside of a permeable container of total thickness l+a, where 'a' is the gas space thickness ($l<x<l+a$), above the coating is shown below. Chlorine dioxide is generated by means of a completely permeable thin film of infinitesimal thickness that lies on top of the coating at x=l.

$$C(x,t) = \sum_{n=0}^{\infty} \frac{Q\alpha_n^2 e^{-bt}\cos(\alpha_n x) \int_0^T e^{b\lambda}e^{-s\lambda}d\lambda}{[l(h-k'\alpha_n^2)^2 + (l+k')\alpha_n^2 + h]\cos(\alpha_n l)}$$

where, $$b=D^c\alpha_n^2,\ k'=4l/P,\ h=D^g/(lD^c)$$

The terms, $\alpha_n$, in the infinite series above are roots of the equation:

$$\alpha \tan(\alpha l) = h - k'\alpha^2$$

$D^c$=Diffusion constant of chlorine dioxide (cm²/sec) in coating $D^g$=Diffusion constant of chlorine dioxide (cm²/sec) in gas phase l=Phenomenological length (cm) of leakage pore $P=C_{coat}(x=l)/C_{gas}(x=l)$=Henry's law constant for partition of the chlorine dioxide between the coating and the gas phase Q=chlorine dioxide generation constant from controlled release film (mole/cm²/sec²)

k=a, the total thickness of the gas layer s=inverse of the time of maximum release rate of chlorine dioxide from the controlled release film C(x,t) is evaluated for a given set of diffusion constants, leakage rate, h, phase partitioning and dimensional constant, k' chlorine dioxide release rate, Q, and inverse relaxation time for release, s, by plotting C($\alpha$) vs $\alpha$ at $t=s^{-1}$. As an example, C(l,t) is calculated for a Petri dish of 62 cm² cross-sectional area of 1 cm total thickness which includes 0.8 cm gas space and 0.2 cm Agar. Since the biologicals are introduced at x=l and grow in the Agar it is important to calculate this concentration. This calculation is necessitated by the strong partitioning of chlorine dioxide into the liquid phase once it is generated by the controlled release film. At the release rates generated by a test film the gas phase concentration was so low (<0.1 ppm) it could not be measured by the detector.

In order to complete the calculation Q, s, P, $D^g$, $D^c$ and l must be assigned or measured. Since Agar is 90% water it is assumed that P=40 can be used [J. J. Kaczur and D. W. Cawlfield, Kirk-othmer Encycl. Chem. Tech. (4th Ed.), 5, 971 (1993)]. $D^c=1.5\times10^{-5}$ cm$^2$/sec and $D^g=0.12$ cm$^2$/sec are reported in the Handbook of Chem. and Phys., 52nd Ed., F47 (1971). In actuality $D^g$ appears in the model only in conjunction with 1 since for the purposes of the calculation $C^g$ is assumed to be uniform in 1<x<1+a.

The leakage flux constant, $D^g/l$, is evaluated by injecting a small quantity (about 10 ppm) of chlorine dioxide into the Petri dish containing no Agar and measuring the chlorine dioxide concentration as a function of time. The Petri dish employed will leak relatively rapidly because of the serrated edges of the bottom dish which is employed to assure good gas exchange necessary for biological growth.

$$(D^g/l)=0.154 \text{ cm/sec}$$

When the source function of the form $Qte^{-bt}$ is integrated from 0 to infinite time, $$\int_0^\infty Qte^{-bt}\,dt = Q/b^2$$

=total moles of chlorine dioxide available
For the purposes of the calculation the controlled release film of density 0.8 gram/cm$^3$ and total volume 0.315 cm$^3$ contains 15 wt. % sodium chlorite of molecular weight 90.44 g mole or $3.35\times10^4$ mole available chlorine dioxide (assuming complete reaction of 5 moles of $ClO_2^{-1}$ to 4 moles chlorine dioxide) and shows a maximum release rate at one day or $s^{-1}=86,400$ sec. This release maximum is typical of an acid releasing film separated from the chlorite containing film by an intermediate wax layer.

Q is thus calculated as $7.23\times10^{-16}$ mole/cm$^2$/sec$^2$ over a 62 cm$^2$ base area Petri dish where the area release rate is assumed to have no lateral dependence over the entire surface of the dish. This is a valid assumption since, even though the controlled release patch occupies a smaller area than the total cross-sectional area of the dish, both the gas and Agar diffusion rates of the chlorine dioxide are large in comparison to the time scale of the release rate.

Figure 10:
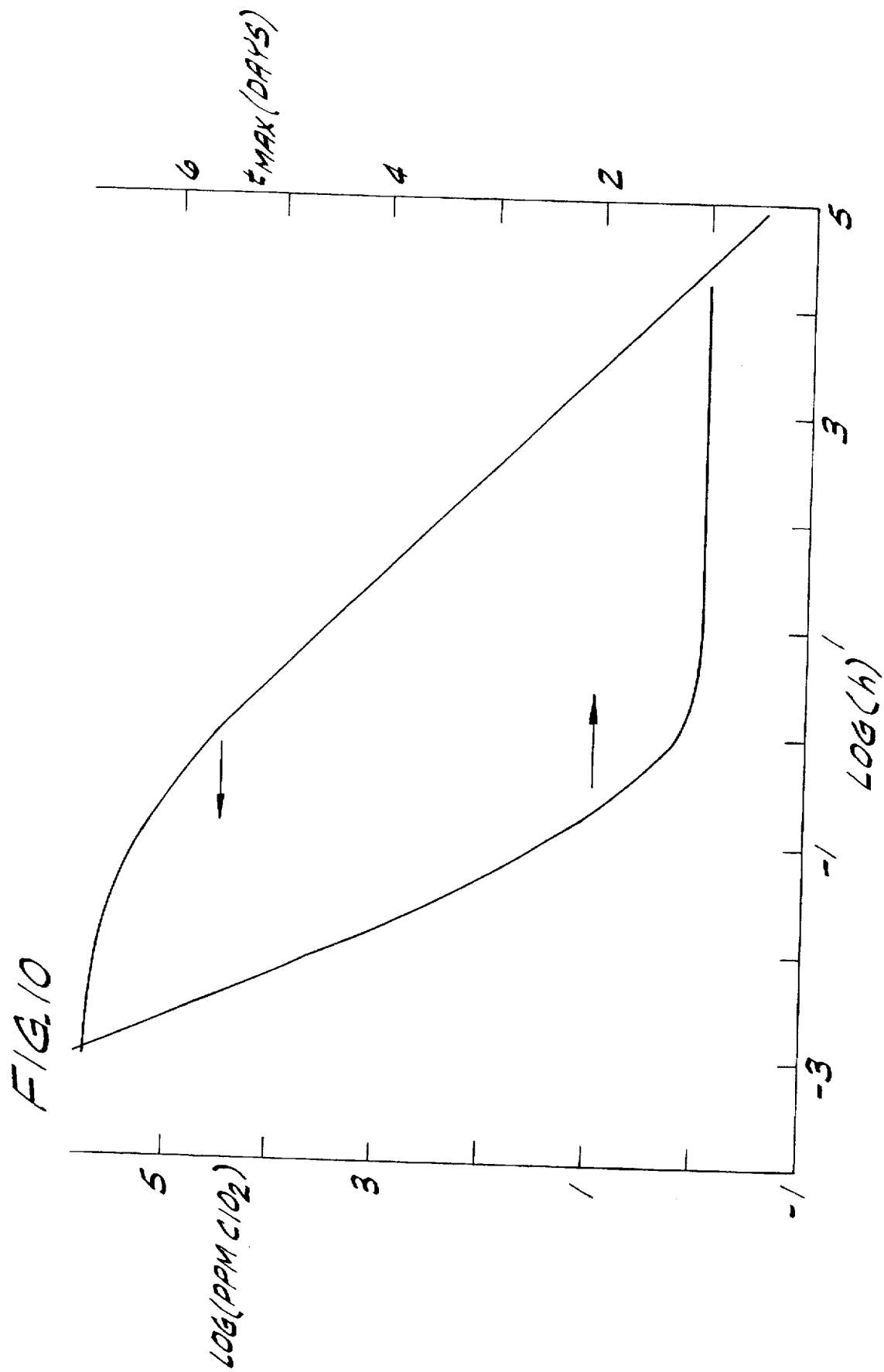
FIG. 10 is a plot of maximum chlorine dioxide concentration as a function of leakage from a container.

The concentration in the gel phase C(l,t) as a function of time is then calculated for a range of leakage rates, h as shown in FIG. 10. At fast leakage rates ($10^5$<h<$10^{-1}$ cm$^{-1}$), the release rate maximizes at $t=s^{-1}$ and the maximum concentration is proportional to h. In essence the concentration at any time significantly greater than the half time for leakage is simply some constant factor multiplied times the source generation rate. However as the leakage rate decreases $10^{-1}$<h<$10^{-5}$, the maximum concentration is generated only at considerably longer time, of course at h=0, no leakage occurs, the maximum concentration is approached asymptotically, and a total of $3.36\times10^{-4}$ moles chlorine dioxide (e.g. $Qs^{-2}\times62$ cm$^2$) is distributed between the 0.2 cm thick gel phase and the 0.8 cm thick gas phase.

For the purposes of estimating how closely the h=0 concentration is approached at h=$8.31\times10^{-4}$ cm$^{-1}$, the concentration in the gel phase at $t=6.0\times10^5$ sec, x=1 ($2.4\times10^{-5}$ mole/cm$^3$) is used to calculate the total amount of chlorine dioxide in the Petri dish.

$$[0.8\ cm(62\ cm^2)l/40)+(0.2\ cm)(62\ cm^2)](2.4\times10^{-5}\ \text{mole/cm}^3)= 3.27\times10^{-4}\ \text{mole}$$

This value is very close to that expected for h=0.

For the leakage rate measured for the Petri dish in which the biological growth experiments are carried out, a maximum concentration of 2.5 ppm is expected in the gel phase at x=1 with a concentration of 0.06 ppm in the gas phase. About 0.25 ppm is required to kill mold spores.

A slightly more complicated environment would be a box of the same dimension as the Petri dish but with its gas space filed with absorbing particles packed with a volume fraction, $\epsilon$=0.5 cm$^3$/cm$^3$. The diffusion of gas through such a composite media has been studied [R. M. Barrer and D. M. Grove, Trans. Far. Soc., 47, 826, 837 (1951); R. Ash and D. M. Grove, Trans. Far. Soc., 56, 1357 (1960)].

The diffusion constant $D^g$ of a gas flowing through a porous media must be replaced by:

$$D^g_p=D^g/[1+(2K_s/r)]$$

where $K_s$=Surface Henry's law coefficient in the relationship $$C_s'=K_sC^g$$

where $C_s'$ is the number of moles of gas absorbed/cm$^2$ of surface and $C^g$ is the gas phase concentration in mole/cm$^3$, r is the equivalent pore radius for a set of axially directed capillaries within a solid having porosity $\epsilon$ and internal surface, A (cm$^2$/cm$^3$), r=2$\epsilon$/A.

For the purposes of the calculation of surface concentration of chlorine dioxide within the porous media, the particles are considered to be small enough so that the concentration of chlorine dioxide throughout the particles' thickness is equilibrated with the gas concentration. For the purposes of this calculation, the entire particle concentration is concentrated in the particle surface.

In this case the surface Henry's law coefficient is related to the bulk coefficient, $K_p$, by $$C^p(1-\epsilon)/A=C_s'=[(1-\epsilon)/A]K_pC^g$$

$$K_s=(1-\epsilon)K_p/A$$

$$D^g_p=D^g/[1+(1-\epsilon/\epsilon)\ K_p]$$

At a porosity of 0.5 and a partition coefficient of 40 into the particles, the diffusion constant for flow through the absorbing porous media would be reduced by a factor of 0.0244. This substantial reduction of apparent gas phase diffusion constant proportionally reduces the leakage rate, h, resulting in a proportional increase in the concentration expected at any time.

The amount, placement and controlled release characteristics required for a biocidal film are estimated where the film is protecting a small 62 cm$^3$ particle filled box which is assumed to leak at the same rate as the Petri dish, h=$8.3\times10^3$ cm$^{-1}$ (a rather good assumption for a typical loosely sealed box). A pallet of well packed, folded (unpacked) boxes might be an analogous case. Since mold spore kill is guaranteed at an exposure of 1 ppm chlorine dioxide for a few minutes, any strategy must generate at least this concentration in a pulsed release in moist regions of the box preferably after several days delay. Destruction of growing mold requires only 0.1–0.5 ppm for a few minutes. The destruction of the growth mechanisms of the cell is so complete that strains with a natural immunity to chlorine dioxide cannot develop. Conveniently, these concentrations are below the human olfactory detection limit of about 10 ppm.

Practically, since such a short exposure is required, a film that released chlorine dioxide in a pulsed fashion would be the ideal system. Of course, depending on the storage environment, this behavior would assure that the initial mold spore infection (originating inside and outside the box) and any subsequent infections (originating outside the box) were destroyed before any growth could occur. A continuous release of 1 ppm thus wastes about 98% of the available chlorite. The preparation of such a film is discussed in Example 16.

Figure 11:
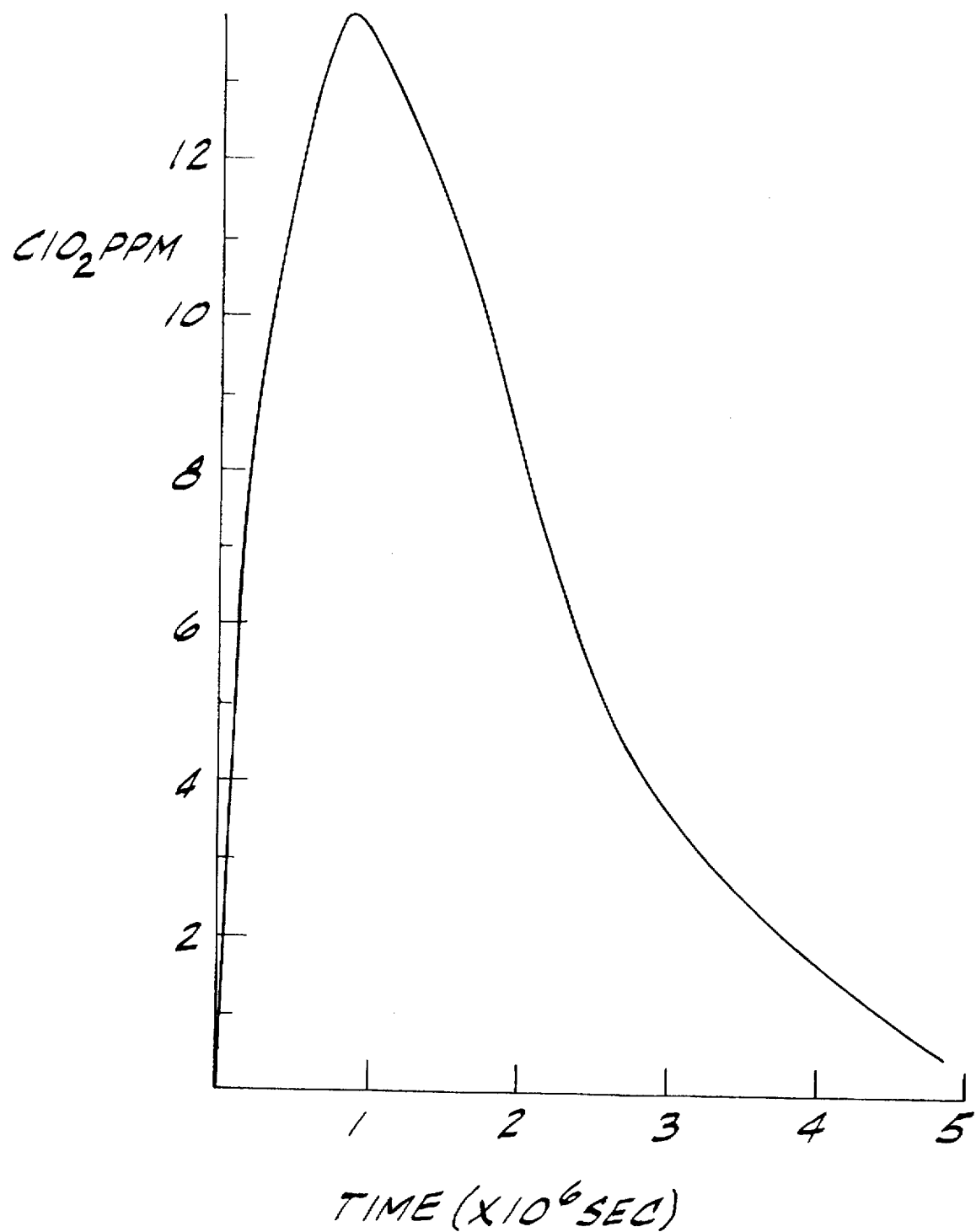
FIG. 11 is a plot of chlorine dioxide concentration as a function of time.

FIG. 11 shows the release characteristics expected for a controlled release film with a maximum release at 10 days, $3.35 \times 10^{-4}$ mole available chlorine dioxide (0.33 cm$^3$ film, 15% wt. % sodium chlorite), placed in a 0.5 porosity box with a bulk Henry's law coefficient of 40 vs air leaking with h=202.76 cm$^{-1}$.

A maximum concentration of 10.4 ppm is reached after 10 days and at least 1 ppm is generated for 0.4 day<t<46 days. Approximately 0.31 cm$^3$ of controlled release material is needed for this purpose. At a materials cost of $1.00/lb, the controlled release material cost required to do the job would be about 0.056 cents. Thus, a box containing 1.1 liters of material could be protected for 1 cent with the above listed parameters.

EXAMPLE 16

The pulsed release capabilities of a multiple layered composite can be calculated as follows to determine whether the composite will provide the desired sustained release rates for a particular application. The time required for complete cation exchange can be predicted from the mobile ion concentration in each layer, $C_i$, wherein i is A, B, or C. In order to determine such a time period, hydronium ion transport across the intermediate layer C is considered to be the rate controlling step, and the diffusion constant and effective mobile ion concentration for hydrogen ion are considered the same in layers A, B and C. Chlorite ion is considered to be relatively immobile and the reaction of chlorite to chlorine dioxide is considered to occur instantaneously once a hydrogen ion enters the hydrophilic layer B.

Hydronium ion mobility in intermediate layer C can be estimated by using experimental data reported by J. L. Crowley et al., J. Poly. Sc., Poly. Phys. Ed., 14, 1769 (1976). Crowley et al. studied the ionic mobility in a graft copolymer of low density polyethylene (79 wt. %) and sulfonated polystyrene (21 wt. %) as a function of ion type, water content and temperature. Sodium, potassium and silver ions travel along polymer bound sulfonate groups by exchange with hydronium cations. At high water contents of 3–6 wt. % phase separation of ion clusters in a hydrophobic matrix is likely. The reported silver ion mobility and mobile ion concentration is quite high under these conditions ($\mu=3.0\times 10^{-4}$ cm$^2$/StatV-sec, C=$3.3\times 10^{-4}$ mol/cc). However, in "dry" films both the mobility and mobile ion concentration decrease substantially ($\mu=1.4\times 10^{-4}$ cm$^2$/StatV-sec, C=$8.3\times 10^{-7}$ mol/cc). The ion diffusion constant D can be calculated from the reported ion mobility using the equation D=(kTμ)/q, where k is Boltzman's constant, T is the absolute temperature, μ is ion mobility and q is electron charge. The calculated ion diffusion constants are $1.21\times 10^{-8}$ cm$^2$/sec and $2.58\times 10^{-8}$ cm$^2$/sec for a dry and wet (6 wt. % water) silver counterion loaded film, respectively.

The morphology of such a copolymer would be very similar to the two material system of the present invention in that both include partially connected ion clusters localized at spherulite boundaries within the hydrophobic layer.

The total amount of hydronium ion that has diffused across boundary AC (moles/cm$^2$) in time t is represented by the function Q:

$$Q(t)/lC_A = (Dt/l^2) - 1/6 - 2(\pi)^{-2} \sum_{n=1}^{\infty} (-1)^n n^{-2} \exp(-Dn^2 \pi^2 t/l^2)$$

Breakthrough of hydronium ion into hydrophilic layer B will occur at $(Dt/l^2)=0.1$ (t=10.4 min, l=5 mil or $1.27\times 10^{-2}$ cm) and steady state diffusion is reached at $(Dt/l^2)=0.45$ (t=46.9 min, l=5 mil). The first two terms in the above equation dominate after steady state is reached. Thus under "wet" conditions (6 wt. % water), $Q(t)=lC_A [(Dt/l^2)-\frac{1}{6}] = 5.72\times 10^{-5}$ mole/day-cm$^2$ at 5 mil thickness. The hydronium ion in a 1 cm$^2$ area film and $1.27\times 10^{-2}$ cm thickness ($1.65\times 10^{-5}$ mole hydronium ion initially) should be almost completely reacted in the chlorite layer in 7 hours. In the "dry" film, which is typical of polyethylene contaminated with ions, $Q(t)=DtC_A/l=6.83\times 10^{-8}$ mole/day-cm$^2$ at 5 mil thickness. Because of the much lower mobile ion concentration, 247 days are required for the hydronium ion to completely diffuse into the hydrophilic layer B. Thus, a multiple layered composite providing from about one day to about 247 days of chlorine dioxide release can be formulated using the two layered composites of the present invention.

The chlorine dioxide release rate is generally rapid when chlorine dioxide release is initiated in a composite containing an intermediate layer because chlorine decomposition is a function of pH. A minimum concentration of hydronium ion is transferred before chlorite decomposition into chlorine dioxide occurs due to the buffering action of the hydrophilic layer containing the chlorite.

The effect of viscosity on reaction rate, the rate of hydration of the film required to produce the minimal amount of free water necessary for catalysis of chlorine dioxide production, and the changing mobile ion concentration and diffusion constant supported by the A, B and C layers can affect hydronium ion transport.

An amount of water must be present in intermediate layer C for transport of hydronium ion. Water is transported through a hydrocarbon matrix as single molecules, except at higher water activities where some tendency to form clusters is noticed. The permeation rate of water through a 5 mil thick high density polyethylene film of 1 cm$^2$ face area would be $6.89\times 10^{-6}$ mole/day/cm$^2$/5 mil (90% RH, 38° C.) as reported by Wessling et al., Encycl. Poly. Sci. Eng., 17, 510 (1989). This permeation rate is significantly less than that seen for polyethylene ionomers which typically contain $3.35\times 10^{-4}$ mole/cc ionic groups at a minimum ($4.08\times 10^{-5}$ mole/day/cm$^2$/5 mil) [Zutty et al., Encycl. Poly. Sci. Tech., 6, 425 (1967)]. The latter ionic content is suitable for layers A, B and C, each of which has the potential to absorb $3.3\times 10^{-4}$ mole/cc×10 moles of water (assuming 10 H$_2$O/H$_3$O$^+$ ion) or $4.2\times 10^{-5}$ mole water/cm$^2$/5 mil (6 wt. % water). Therefore, 5 mil A and B layers would require about 1 day to saturate to 6% water from an initially dry state. At most, an additional day would then be required to saturate the intermediate layer C.

EXAMPLE 17

In order to make a hydrophobic propylene glycol monostearate acid releasing wax on a laboratory scale, propylene glycol monostearate (200 g) was melted in a dry, stoppered, 2-liter schlenk at 50°–60° C. using a heating mantle. The melt was stirred at constant temperature under reduced pressure for three to four hours to remove residual moisture. When bubbling of the melt under vacuum ceased, the schlenk was flushed and maintained with dry nitrogen gas.

Phosphorus pentoxide (27.7 g) was loaded into a powder addition funnel in a glove bag continuously purged with dry nitrogen. The funnel was connected to the schlenk under flowing nitrogen, and the phosphorus pentoxide was gradually added to the melt using a screw feeder over three or four hours as the melt was stirred rapidly at 50°–60° C. under dry nitrogen. After the addition, the melt was stirred under dry nitrogen gas for at least four hours.

Tetraethyl orthosilicate (TEOS; 39 ml) was then added slowly over 40 minutes using an addition funnel. Ethanol by-product was vented through a septum and needle inserted at the top of the addition funnel. After the TEOS addition, remaining ethanol was pumped off under reduced pressure for about 12 hours while minimizing foaming and maintaining a temperature sufficient to volatilize ethanol condensed on the schlenk walls. The resulting propylene glycol monostearate acid releasing wax was then allowed to solidify at room temperature in the glove bag under dry nitrogen.

EXAMPLE 18

In order to make a hydrophobic propylene glycol monostearate acid releasing wax on a commercial scale, propylene glycol monostearate (1225.5 lbs.) was melted at 55° C. using oil heating in a stainless steel stirred tank jacketed reactor with internal cooling coils and a reflux condenser/receiver system. Powdered phosphorus pentoxide (170.2 lbs.) was introduced gradually over three to four hours with cooling. After the reaction proceeded for four to six hours at 55° C., tetraethyl orthosilicate (221.3 lbs) was added to the tank and allowed to react for 12 hours under vacuum. The propylene glycol monostearate acid releasing wax was collected from the bottom of the reactor and allowed to solidify at room temperature.

EXAMPLE 19

A chlorine dioxide-releasing powder was prepared on a laboratory scale. Sodium chlorite flakes (Vulcan Chemicals) were ground to a powder and vacuum dried overnight in a schlenk. Sodium chlorite (10 g), sodium sulfate (775 g; less than 125 μm particle size), the propylene glycol monostearate acid releasing wax of Example 17 (130 g), and Petrowax 3040 microcrystalline wax (90 g) were each placed in a flask and stoppered inside a large glove bag with a Ross mixer under dry nitrogen gas. The mixing bowl was heated to 53° C. with a circulating bath. The glove bag and mixing bowl were purged with dry nitrogen. The Petrowax was then added to the bowl and melted. The sodium chlorite was added to the melted wax and mixed for two minutes. 400 g of the sodium sulfate was added and mixed for two minutes, and then the propylene glycol monostearate acid releasing wax was added and mixed for two minutes. The remaining sodium sulfate was added and mixed for five minutes. The product was collected in an airtight bag under nitrogen with desiccant and cooled overnight. The cooled material was cryogenically ground to a powder and stored.

EXAMPLE 20

Another chlorine dioxide-releasing powder was prepared on a laboratory scale. Sodium chlorite flakes (Vulcan Chemicals) were ground to a powder and vacuum dried overnight in a schlenk. Sodium chlorite (10 g), calcium sulfate (775 g), the propylene glycol monostearate acid releasing wax of Example 17 (130 g), and Petrowax 3040 microcrystalline wax (90 g) were each placed in a flask and stoppered inside a large glove bag with a Ross mixer under dry nitrogen gas. The mixing bowl was heated to 53° C. with a circulating bath. The glove bag and mixing bowl were purged with dry nitrogen. The Petrowax was then added to the bowl and melted. The sodium chlorite was added to the melted wax and mixed for three minutes. Half of the calcium sulfate was added and mixed for three minutes, and then the propylene glycol monostearate acid releasing wax was added and mixed for two minutes. The remaining calcium sulfate was added and mixed for five minutes. The product was collected in an airtight bag under nitrogen with desiccant and cooled overnight. The cooled material was cryogenically ground to a powder and stored.

EXAMPLE 21

A powder providing sustained release of chlorine dioxide was prepared by melting Petrowax 3040 microcrystalline wax (90 g) in a planetary mixer. Sodium chlorite (10 g) was added to the melted wax and mixed for about two minutes. Sodium sulfate (385 g) was added and mixed for about two minutes. Propylene glycol monostearate acid releasing wax of Example 18 (130 g) was then added and mixed for about two minutes. Sodium sulfate (385 g) was poured into the mixer and mixed for about 5 minutes. The product was collected under dry conditions and cooled at room temperature overnight. The cooled material was cryogenically ground to a powder and stored.

Controlled release of chlorine dioxide over several days is accomplished at varying temperature and humidity conditions ranging from about 70–80° F. and about 25–50% relative humidity. Chlorine dioxide release rates are dependent on both temperature and relative humidity.

EXAMPLE 22

A powder providing sustained release of chlorine dioxide was prepared by melting Petrowax 3040 microcrystalline wax (90 g) in a planetary mixer. Sodium chlorite (40 g) was added to the melted wax and mixed for about two minutes. Sodium sulfate (155 g) was added and mixed for about two minutes. Propylene glycol monostearate acid releasing wax of Example 18 (560 g) was then added and mixed for about two minutes. Sodium sulfate (155 g) was poured into the mixer and mixed for about 5 minutes. The product was collected under dry conditions and cooled at room temperature overnight. The cooled material was cryogenically ground to a powder and stored.

Controlled release of chlorine dioxide over several days is accomplished at about 80° F. and 45%. relative humidity.

EXAMPLE 23

A powder providing sustained release of chlorine dioxide is prepared by melting a carboxylate of a poly α-hydroxy alcohol such as sorbitan monostearate in a planetary mixer. A chlorite anion source such as sodium chlorite is added to the melt and mixed for about two minutes. Sodium sulfate is then added and mixed for about two minutes. The product is collected under dry conditions and cooled at room temperature overnight. The cooled material is cryogenically ground to a powder and stored.

A precursor of such a powder was formed by melting sorbitan monostearate in a planetary mixer, adding sodium chlorite to the melt and mixing for about two minutes. The melt was white after addition of sodium chlorite, indicating that chlorine dioxide was not generated in the melt. A color change from white to yellow was observed as the melt was heated, indicating generation of chlorine dioxide in the melt.

Observations are reported in Table 5 below:

TABLE 5

| No. | ARA Wt.[1] | NaClO$_2$ Wt. | T (° C.)[2] | t (min)[3] | color[4] | dry N$_2$[5] |
|---|---|---|---|---|---|---|
| 1 | 10 g (90.7%) | 1.0 g (9.3%) | 65 | 30 | BY | Yes |
| 2 | 5.1 g (90.8%) | 0.51 g (9.2%) | 60 | 10 | SY | Yes |
| 3 | 5.0 g (90.9%) | 0.50 g (9.1%) | 61 | 40 | SY | No |
| 4 | 2.0 g (90.4%) | 0.22 g (9.6%) | 61 | 5 | W | No |
| 5 | 1.0 g (90.8%) | 0.10 g (9.2%) | 62–65 | 10 30 50 | W W BY | No |
| 6 | 3.0 g (90.8%) | 0.30 g (9.2%) | 62 | 4 | SY | No |
| 7 | 3.0 g (89.9%) | 0.34 g (10.1%) | 65 | 5 8 10 | W W SY | No |

[1]ARA = acid releasing agent (i.e., sorbitan monostearate)
[2]Temperature at which melt was heated
[3]Time period after which color of melt was observed
[4]Color observed: BY (Bright Yellow); SY (Slight Yellow); W (White)
[5]Whether dry nitrogen atmosphere was used during preparation Chlorine dioxide was not released from preparation nos. 5 and 7 until after thirty minutes and eight minutes, 20 respectively. Thus, sorbitan monostearate is a viable acid releasing acid for use in preparing powders of the invention.

EXAMPLE 24

A chlorine dioxide-releasing liquid was prepared on a laboratory scale and used to coat seeds. Sodium chlorite (0.2248 g), sodium sulfate (1.2684 g), the propylene glycol monostearate acid releasing wax of Example 17 (1.5786 g), and Petrowax 3040 microcrystalline wax (0.3224 g) were each placed in a test tube and stoppered inside a large glove bag with a vortex mixer and stirring/hot plate under dry nitrogen gas. The plate was heated to about 55° C. with an oil bath. The glove bag was purged with dry nitrogen. The Petrowax was then melted by placing the test tube in the oil bath. The sodium chlorite was added to the melted wax and mixed thoroughly. The sodium sulfate was added and mixed thoroughly, and then the propylene glycol monostearate acid releasing wax was added. The test tube was stoppered, removed from the glove bag. The melt solidified upon cooling.

The test tube containing the solid was returned to the glove bag and heated in the oil bath for about 30 seconds to melt the solid. Corn seeds were also placed within the glove bag under nitrogen. The melt was spread onto an aluminum pan heated to about 48° C. using a thermal pyrometer and surface probe. The corn seeds were placed on the melt and were dipped in the melt to achieve a partial coating. Sustained release of chlorine dioxide was observed over several days.

While the invention is susceptible to various modifications and alternative forms, specific embodiments thereof have been shown by way of example in the drawings and have been described herein in detail. It should be understood, however, that it is not intended to limit the invention to the particular form disclosed, but on the contrary, the intention is to cover all modifications, equivalents and alternatives falling within the spirit and scope of the invention as defined by the appended claims.

We claim:

1. A composite for retarding, killing, preventing or controlling microbiological contamination comprising:

a hydrophilic material containing an α-amino ether, α-amino alcohol, or α-amino ester and a chlorite salt; and a hydrophobic material containing an acid releasing agent, the hydrophilic and hydrophobic materials being adjacent and substantially free of water, the hydrophilic material being capable of generating and releasing chlorine dioxide after hydrolysis of the acid releasing agent.

2. The composite of claim 1 wherein the α-amino ether, α-amino alcohol, or α-amino ester and the chlorite salt are formed by reaction of an iminium chlorite and a base selected from the group consisting of a metal alkoxide, an ammonium alkoxide, a metal oxide, a metal carboxylate, and an ammonium carboxylate.

3. The composite of claim 1 wherein the hydrophilic material further includes urea.

4. The composite of claim 1 wherein the hydrophilic material further includes a plasticizer selected from the group consisting of N-methylacetamide, formamide, succinamide, N-ethylacetamide, N-methylformamide, N-ethylformamide, acrylamide, isopropylacrylamide-acrylamide, and amido substituted alkylene oxides.

5. The composite of claim 1 wherein the chlorite salt is selected from the group consisting of an alkali metal chlorite, an alkaline-earth metal chlorite, and a chlorite salt of a transition metal ion or a protonated primary, secondary, tertiary or quaternary amine.

6. The composite of claim 1 wherein the hydrophilic material further includes urea and a plasticizer selected from the group consisting of N-methylacetamide, formamide, succinamide, N-ethylacetamide, N-methylformamide, N-ethylformamide, acrylamide, isopropylacrylamide-acrylamide, and amido substituted alkylene oxides.

7. The composite of claim 1 wherein the hydrophobic material includes a diluent selected from the group consisting of a microcrystalline wax, a paraffin wax, a synthetic wax, and a polymer.

8. The composite of claim 1 wherein the hydrophobic material comprises between about 10 wt. % and about 100 wt. % of the acid releasing agent, up to about 80 wt. % of a diluent, and up to about 60 wt. % of the plasticizer.

9. The composite of claim 8 wherein the hydrophobic material comprises between about 40 wt. % and about 100 wt. % of the acid releasing agent, between about 20 wt. % and about 80 wt. % of the diluent, and up to about 20 wt. % of the plasticizer.

10. The composite of claim 8 wherein the acid releasing agent includes a carboxylic acid, an ester, an anhydride, an acyl halide, phosphoric acid, a phosphate ester, a trialkylsilyl phosphate ester, a dialkyl phosphate, sulfonic acid, a sulfonic acid ester, a sulfonic acid chloride, a phosphosilicic anhydride, a phosphosilicate, a phosphosiloxane or a carboxylate of a poly α-hydroxy alcohol; the diluent is selected from the group consisting of a microcrystalline wax, a paraffin wax, a synthetic wax, and a polymer; and the plasticizer is selected from the group consisting of N-methylacetamide, formamide, succinamide, N-ethylacetamide, N-methylformamide, N-ethylformamide, acrylamide, isopropylacrylamide-acrylamide, and amido substituted alkylene oxides.

11. A composite for retarding, killing, preventing or controlling microbiological contamination comprising:

a hydrophilic material containing an α-amino ether, α-amino alcohol, or α-amino ester, a chlorite salt, and an amide; and a hydrophobic material containing an acid releasing agent, the hydrophilic and hydrophobic materials being adjacent and substantially free of water, the hydrophilic material being capable of generating and releasing chlorine dioxide after hydrolysis of the acid releasing agent.

12. The composite of claim 11 wherein the acid releasing agent includes a carboxylic acid, an ester, an anhydride, an acyl halide, phosphoric acid, a phosphate ester, a trialkylsilyl phosphate ester, a dialkyl phosphate, sulfonic acid, a sulfonic acid ester, a sulfonic acid chloride, a phosphosilicic anhydride, a phosphosilicate, a phosphosiloxane or a carboxylate of a poly α-hydroxy alcohol.

13. The composite of claim 11 wherein the chlorite salt is selected from the group consisting of an alkali metal chlorite, an alkaline-earth metal chlorite, and a chlorite salt of a transition metal ion or a protonated primary, secondary, tertiary or quaternary amine.

14. The composite of claim 12 wherein the hydrophobic material includes a diluent selected from the group consisting of a microcrystalline wax, a paraffin wax, a synthetic wax, and a polymer.

15. The composite of claim 11 wherein the amide is selected from the group consisting of urea, N-methylacetamide, formamide, succinamide, N-ethylacetamide, N-methylformamide, N-ethylformamide, isopropylacrylamide-acrylamide, and amido substituted alkylene oxide.

* * * * *